(12) United States Patent
Keteyian et al.

(10) Patent No.: US 10,335,083 B2
(45) Date of Patent: Jul. 2, 2019

(54) SYSTEMS AND METHODS FOR DETECTING AND ANALYZING BIOSIGNALS

(71) Applicants: Courtland Keith Keteyian, Ann Arbor, MI (US); Jinyong Kim, Blue Bell, PA (US)

(72) Inventors: Courtland Keith Keteyian, Ann Arbor, MI (US); Jinyong Kim, Blue Bell, PA (US)

( * ) Notice: Subject to any disclaimer, the term of this patent is extended or adjusted under 35 U.S.C. 154(b) by 214 days.

(21) Appl. No.: 15/216,108

(22) Filed: Jul. 21, 2016

(65) Prior Publication Data

US 2017/0020454 A1    Jan. 26, 2017

Related U.S. Application Data

(60) Provisional application No. 62/195,060, filed on Jul. 21, 2015.

(51) Int. Cl.
*A61B 5/04*    (2006.01)
*A61B 5/00*    (2006.01)
(Continued)

(52) U.S. Cl.
CPC .......... *A61B 5/6803* (2013.01); *A61B 5/0022* (2013.01); *A61B 5/02055* (2013.01);
(Continued)

(58) Field of Classification Search
USPC ................................................. 600/300–301
See application file for complete search history.

(56) References Cited

U.S. PATENT DOCUMENTS

| 4,133,604 A | 1/1979 | Fuller |
| 6,556,852 B1 | 4/2003 | Schulze et al. |

(Continued)

FOREIGN PATENT DOCUMENTS

EP    2238902    3/2010

OTHER PUBLICATIONS

Yazaki et al., "Portable Life Support System Using Wearable Biosensor Worn by the Elderly," Tokyo University of Technology, ICROS-SICE International Joint Conference 2009 Aug. 18-21, 2009, Fukuoka International Congress Center, Japan.
(Continued)

*Primary Examiner* — Nicole F Lavert
(74) *Attorney, Agent, or Firm* — Aurora Counsulting LLC; Ashley Sloat

(57) ABSTRACT

A system for monitoring biosignals of a user includes a first end region, positionable proximate a first ear of a user and including a first sensor array; a second end region, positionable proximate a second ear of the user and including a second sensor array; an intermediate region, positionable on a neck region of the user; a coupling element configured to couple the first and second end regions to the intermediate region; and a first attachment element and a second attachment element. The first attachment element couples the first end region to a head-mounted accessory and the second attachment element couples the second end region to the head-mounted accessory. The first end region includes a first electrode and the second end region includes a second electrode, such that there is a fixed distance between the first and second electrodes.

20 Claims, 13 Drawing Sheets

(51) Int. Cl.
| | |
|---|---|
| *A61B 5/0205* | (2006.01) |
| *G16H 40/67* | (2018.01) |
| *A61B 5/029* | (2006.01) |
| *A61B 5/0402* | (2006.01) |
| *A61B 5/0488* | (2006.01) |
| *A61B 5/0476* | (2006.01) |
| *A61B 7/00* | (2006.01) |
| *A61B 5/16* | (2006.01) |
| *A61B 5/1455* | (2006.01) |
| *A61B 5/021* | (2006.01) |
| *A61B 5/024* | (2006.01) |
| *A61B 5/053* | (2006.01) |
| *A61B 5/113* | (2006.01) |
| *A61B 5/087* | (2006.01) |
| *A61B 5/11* | (2006.01) |
| *A61B 5/01* | (2006.01) |
| *A61B 5/08* | (2006.01) |

(52) U.S. Cl.
CPC ............... *G16H 40/67* (2018.01); *A61B 5/01* (2013.01); *A61B 5/021* (2013.01); *A61B 5/029* (2013.01); *A61B 5/02405* (2013.01); *A61B 5/04001* (2013.01); *A61B 5/0402* (2013.01); *A61B 5/04008* (2013.01); *A61B 5/0476* (2013.01); *A61B 5/0488* (2013.01); *A61B 5/0533* (2013.01); *A61B 5/0537* (2013.01); *A61B 5/087* (2013.01); *A61B 5/0816* (2013.01); *A61B 5/1112* (2013.01); *A61B 5/1135* (2013.01); *A61B 5/14552* (2013.01); *A61B 5/165* (2013.01); *A61B 5/443* (2013.01); *A61B 5/4803* (2013.01); *A61B 5/4866* (2013.01); *A61B 5/7282* (2013.01); *A61B 7/00* (2013.01); *A61B 2562/0209* (2013.01)

(56) References Cited

U.S. PATENT DOCUMENTS

| | | | |
|---|---|---|---|
| 2003/0135127 | A1 | 1/2003 | Sackner et al. |
| 2003/0214408 | A1 | 11/2003 | Grajales et al. |
| 2008/0287770 | A1 | 11/2008 | Kurzweil et al. |
| 2011/0087115 | A1 | 4/2011 | Sackner et al. |
| 2012/0316624 | A1* | 12/2012 | Smith ............... A61F 7/007 607/99 |
| 2013/0063929 | A1* | 3/2013 | Borden ............... G02C 11/04 362/103 |
| 2013/0072765 | A1 | 3/2013 | Kahn et al. |
| 2016/0054569 | A1 | 2/2016 | Lewis |

OTHER PUBLICATIONS

Poh et al., "Cardiovascular Monitoring Using earphones and a Mobile Device," MIT Media Lab, Pervasive Computing Oct.-Dec. 2012, 18-26.

Asada et al., "Mobile Monitoring with Wearable Photoplethysmographic Biosensors," Massachusetts Institute of Technology, IEEE Engineering in Medicine and Biology Magazine, 2003, 28-40.

Turner, "Biosensors: sense and sensibility", Chem. Soc. Rev., 2013, 42 (8), 3184-3196.

\* cited by examiner

SYSTEMS AND METHODS FOR DETECTING AND ANALYZING BIOSIGNALS

CROSS-REFERENCE TO RELATED APPLICATIONS

This patent application claims priority to U.S. provisional patent application Ser. No. 62/195,060, filed on Jul. 21, 2015, which is herein incorporated by reference in its entirety.

INCORPORATION BY REFERENCE

All publications and patent applications mentioned in this specification are herein incorporated by reference in their entirety, as if each individual publication or patent application was specifically and individually indicated to be incorporated by reference in its entirety.

TECHNICAL FIELD

This disclosure relates generally to the digital health field, and more specifically to new and useful systems and methods for detecting and analyzing biosignals.

BACKGROUND

Hospital readmissions are expensive and negatively impact patients and hospitals. According to the Healthcare Cost and Utilization Project, in 2011, Medicare paid for 58% of readmissions related to the four most common health conditions, followed by private insurance (20%) and Medicaid (18%) (Fingar, K. and Washington, R. 2015. "Trends in Hospital Readmissions for Four High-Volume Conditions, 2009-2013."). Thirty-seven percent of the total Medicare budget is spent on hospital readmissions. In 2013, there were about 500,000 readmissions totaling $7 billion in aggregate hospital costs for the following conditions: acute myocardial infarction (AMI), congestive heart failure (CHF), chronic obstructive pulmonary disease (COPD), and pneumonia. Further, repeated hospitalizations or readmissions increase stress and complications such as hospital acquired infections.

Patient populations experiencing significant hospital readmission include the elderly population and those in lower socioeconomic groups. These and other demographics are less inclined to adopt wearable health-monitoring technologies due to several factors including: inconvenience, relevance, consistency in sensor placement, and discomfort.

Currently available systems for monitoring patient well-being post-hospitalization include wearable devices for monitoring respiration, heart-related parameters (e.g., heart rate), and/or patient input parameters (e.g., weight, general feeling, patient-reported symptoms, etc.). These devices are cumbersome, intrusive (e.g., in a patient's nose, around the chest, etc.), uncomfortable, difficult to position in the same location during each measurement period, and/or limited in their ability to measure a patient's wellbeing. Further, currently available systems require the user to purchase a new accessory that is compatible with the system and/or to wear an accessory comprising the system that the user does not typically wear.

In accordance with these and other deficiencies of current devices and technologies, there is a need for new and useful systems and methods for detecting and analyzing biosignals that can be readily adopted by a wide variety of demographics, including demographics less inclined to adopt biosignal sensing technology. Further, there is a need for new, useful, and inexpensive systems and methods that promote and improve general health and wellbeing to reduce healthcare costs. This disclosure provides such new and useful systems and methods for detecting and analyzing biosignals.

SUMMARY

There is a need for new and useful systems and methods for health monitoring. In particular, there is a need for systems and methods that enable sensor measurements to be taken reliably over time to determine a health condition of a user. The present disclosure provides such embodiments for biosignal measurement and monitoring.

One aspect of the present disclosure is directed to a system for monitoring biosignals of a user. In some embodiments, the system includes: a first end region, positionable proximate a first ear of a user and including a first sensor array; a second end region, positionable proximate a second ear of the user and including a second sensor array; an intermediate region, positionable on a neck region of the user, a coupling element configured to couple the first and second end regions to the intermediate region; and a first attachment element and a second attachment element, wherein the first attachment element couples the first end region to a head-mounted accessory and the second attachment element couples the second end region to the head-mounted accessory.

In some embodiments, each attachment element comprises a sleeve defining an aperture configured to slidably receive a temple or temple end of the head-mounted accessory. In some embodiments, a diameter of the aperture defined by the sleeve is adjustable.

In some embodiments, the coupling element electrically and physically couples the first and second end regions to the intermediate region.

In some embodiments, the system further includes a first electrode positioned on or embedded within the first end region and a second electrode positioned on or embedded within the second end region. In some such embodiments, there is a fixed distance between the first and second electrodes. In some embodiments, the fixed distance is a linear distance between two ears of the user that measures less than one foot.

In some embodiments, the first and second sensor arrays are configured to cooperatively detect an impedance of an applied current along a distance separating the first and second sensor arrays, thereby providing a measurement of ionic fluid content within the user.

In some embodiments, the system further includes a head-mounted accessory. In some such embodiments, the head-mounted accessory is one of: eyeglasses, sunglasses, goggles, and bifocals. In some embodiments, the first and second sensor arrays are integrated into the head-mounted accessory.

In some embodiments, the system further includes a processor and a computer-readable medium having non-transitory, processor-executable instructions stored thereon. In some embodiments, the processor is integrated into one of: the first end region, the second end region, and the intermediate region. Further, in some embodiments, execution of the instructions on the computer-readable medium causes the processor to perform a method including: acquiring a first biosignal from a first body region of the user using the first sensor array, acquiring a second biosignal from a second body region of the user using the second sensor array, extracting a first feature from the first biosignal and a second feature from the second biosignal, and analyzing the first and second features to determine a health condition of the user.

In some embodiments, the method performed by the processor further includes: monitoring the health condition of the user over time using one or more of the first and second sensor arrays; and identifying a change in the health condition over time.

In some embodiments, the method performed by the processor further includes: transmitting, using an antenna, one or more of the first and second features to a healthcare provider.

In some embodiments, the first and second biosignals include one or more of: bioimpedance signals, temperature signals, pulse oximetry signals, blood flow, blood pressure, heart rate, heart rate variability, electrocardiography, electromyography, electroencephalography signals, galvanic skin response, magnetoencephalography impedance signals, acoustic signals, respiration signals, positional signals, and caloric intake signals.

In some embodiments, the first and second features include one or more of: a blood volume, a blood pressure, a skin water content, cardiac output, an average temperature, an instantaneous temperature, an oxygen saturation level, a heart rate, a heart rate variability, a heart electrical activity, a brain electrical activity, a muscle electrical activity, a stress level, a neuronal activity level, a depth of breadth, a respiration rate, thoracic variations, inspiratory flow characteristics, expiratory flow characteristics, vocal sounds, a location of the user, and a calorie intake amount.

In some embodiments, the first body region is contralateral the first sensor array and the second body region is contralateral the second sensor array. In some embodiments, the first body region is ipsilateral the first sensor array and the second body region is ipsilateral the second sensor array. In some embodiments, the first body region is the same as the second body region.

Another aspect of the present disclosure is directed to a system for monitoring biometric signals from the head region of a user that can be coupled to eyewear with first and second legs, with the eyewear to be worn by a user. In some embodiments, the system includes: a first end region including a first sensor array and a first housing that couples to the first leg, and a second end region including a second sensor array and a second housing that couples to the second leg. In some embodiments, the first and second sensor arrays are each held substantially in place on either side of the head of the user, spatially separated by a linear distance that measures less than one foot. In some embodiments, the first and second sensor arrays are each configured to detect a biometric signal at their respective sensor-user interfaces proximal to where the pinnae and the temporal bones of the user meet. In some embodiments, the system further includes an intermediate region configured to communicate with and process signals detected by the first and second sensor arrays.

In some embodiments, each sensor array includes a single electrode enclosed within the respective housings, configured to deliver and measure characteristics of electrical signals.

In some embodiments, the first and second sensor arrays are configured to cooperatively detect the impedance of an applied current along the distance separating the two sensor arrays through the tissue, and thereby providing a measurement of ionic fluid content within the user.

In some embodiments, the first and second housings include material that surrounds the legs to permit coupling of the first and second end regions to the first and second legs, respectively.

In some embodiments, the system further includes a coupling element to couple the first and second end regions to the intermediate region. In some such embodiments, the coupling element is a lanyard. In some embodiments, the body of the coupling element includes supplementary sensor arrays configured to sense additional biometric signals.

In some embodiments, the first and second housings include an adhesive to permit coupling of the first and second end regions to the first and second legs.

In some embodiments, the system further includes: a first wireless signal transmitter enclosed within the first end region; a second wireless signal transmitter enclosed within the second end region; and a wireless signal receiver integrated with the intermediate region.

In some embodiments, the first and second end regions are positioned where each of the legs contacts the skin on the tops of each of the pinnae where the pinnae make contact with the head, such that the electrodes make direct contact with the skin.

In some embodiments, the first and second end regions are positioned where the medial side of each of the legs faces the skin, posterior to where each of the pinnae make contact with the head, such that the electrodes make direct contact with the skin.

Another aspect of the present disclosure is directed to a system for measuring a set of biosignals of a user wearing headwear where a pressure is generated between the user and the headwear. In some embodiments, the system includes: a housing coupled to the user's headwear and configured to enclose system components and receive an amount of the pressure that is generated between the user and the user's headwear; a first sensor array that is substantially sustained by the housing in a stationary position proximate to the user's skin surface; a second sensor array that is substantially sustained by the housing in a stationary position proximate to the user's skins surface. In some embodiments, the second sensor array and the first sensor array are separated by a substantially similar distances across measurements of the set of biosignals of the user.

Another aspect of the present disclosure is directed to a physiological monitoring apparatus that can be coupled to a pair of eyewear having a first leg and a second leg and worn over the ears of a user. In some embodiments, the system includes: a first and second sensor array configured to send electrical signals between the ears of the user and sense electrophysiological signals from the skin tissue substantially adjacent to the ears of the user; a first housing configured to fasten to the first leg of the eyewear and to position the first sensor array to stay in contact with the skin tissue substantially adjacent to one ear of the user; a second housing configured to fasten to the second leg of the eyewear and to position the second sensor array to stay in contact with the skin tissue substantially adjacent to the other ear of the user; and an intermediate region in communication with the first and second sensor arrays.

In some embodiments, the first and second sensor arrays include bioimpedance sensors configured to monitor the body fluid status of the user.

In some embodiments, the electrical signals are generated continuously and the electrophysiological signals are acquired continuously.

In some embodiments, the first housing and the second housing are made of electrically insulating materials.

In some embodiments, the intermediate region includes an analog-to-digital converter for receiving and digitizing the electrophysiological signals acquired by the first and second sensor arrays.

In some embodiments, the intermediate region further includes a processor configured to perform an analysis and translation of the digitized electrophysiological signals into a physiological measurement data.

In some embodiments, the intermediate region includes a transmission module configured to perform signal transmission.

In some embodiments, the intermediate region includes a power module configured to supply power to the apparatus.

In some embodiments, the system further includes an external device. In some such embodiments, the external device is in communication with the intermediate region through the transmission module. Further, in some such embodiments, the external device is a mobile phone.

In some embodiments, the system further includes an environmental sensor supported by one of the first housing and the second housing and configured to detect the environment conditions in the vicinity of the user.

In some embodiments, the first sensor array is positioned to stay in contact with the skin tissue on top of a first ear of the user and the second sensor array is positioned to stay in contact with the skin tissue around the posterior area of a second ear of the user.

In some embodiments, the first housing includes a first attachment element adapted to secure the first housing to the first leg of the eyewear and the second housing includes a second attachment element adapted to secure the second housing to the second leg of the eyewear.

In some embodiments, the system further includes a coupling element. In some such embodiments, the coupling element includes a strap adapted to connect the first housing and the second housing. Further, in some such embodiments, the length of the strap is adjustable.

In some embodiments, the intermediate region is connected with the first housing and the second housing via the coupling element. In some such embodiments, the position of the intermediate region on the coupling element is adjustable.

Another aspect of the present disclosure is directed to a physiological monitoring apparatus that can be coupled to a pair of eyewear having a first leg and a second leg and worn over the ears of a user. In some embodiments, the system includes: a first sensor array and a second sensor array configured to send electrical signals between the ears of the user and sense electrophysiological signals from the skin tissue substantially adjacent to the ears of the user; a first housing configured to fasten to the first leg of the eyewear and to position the first sensor array to stay in contact with the skin tissue substantially adjacent to one ear of the user; a second housing configured to fasten to the second leg of the eyewear and to position the second sensor array to stay in contact with the skin tissue substantially adjacent to the other ear of the user; and an intermediate region in communication with the first and second sensor arrays.

In some embodiments, the intermediate region includes: an analog to digital converter for receiving and digitizing the electrophysiological signals acquired by the first and second sensor arrays; a processor configured to perform an analysis and translation of the digitized electrophysiological signals into physiological measurement data; a transmission module configured to perform signal transmission; and a power module configured to supply power to the apparatus.

Another aspect of the present disclosure is directed to a method taught to a user by a prescriber to achieve daily physiological monitoring of ionic fluid content changes within the body of a user, the user wearing eyewear with first and second legs daily. In some embodiments, the method includes: coupling to the eyewear a physiological monitoring device including a first and second end region that senses a biometric signal; and utilizing the device to: generate a current through a linear distance of the body of the user and between the first and second end regions. In some embodiments, the first end region is coupled to the first leg, and the second end region is coupled to the second leg, such that the first end region is contralateral to the second end region on the opposite side of the head of the user when the eyewear is worn by the user. In some embodiments, the linear distance measures less than one foot.

In some embodiments, the method includes: sensing an impedance of the current through the linear distance; storing the impedance measurement in a computer-readable medium; repeating the steps of generating a current, sensing the impedance of the current, and storing the impedance measurement over a set of time points defined by the prescriber; and generating a comparative metric by calculating a numerical difference between sequential impedance measurements stored within the computer-readable medium.

In some embodiments, the method further includes detecting a separate biometric signal at a supplementary sensor array configured to enable detection of additional biometric signals.

Another aspect of the present disclosure is directed to a method for measuring biosignals of a user wearing headwear where a pressure is generated between the user and the headwear. In some embodiments, the method includes: receiving, at the first and second end regions, an amount of the pressure generated between the headwear and the user, interfacing with the user's head at a first location by a first sensor array substantially sustained proximal to the first location over a set of time points; interfacing with the user's head at a second location by a second sensor array substantially sustained proximal to the second location over the set of time points; receiving a set of biosignals at the first sensor array and at the second sensor array when the first sensor array and the second sensor array are separated by a substantially similar distance over the set of time points; and communicating data that is based on the set of biosignals.

Another aspect of the present disclosure is directed to a method for monitoring physiological signals of a user wearing a pair of eyewear having a first leg and a second leg. In some embodiments, the method includes: sensing electrophysiological signals with a first and second sensor array; digitizing the electrophysiological signals with an analog to digital converter, processing the digitized electrophysiological signals into physiological measurement data with a processor; and transmitting the physiological measurement data to an external device.

In some embodiments, the first sensor array is positioned to stay in contact with the skin tissue substantially adjacent to a first ear of the user via a first housing fastened to the first leg of the eyewear and the second sensor array is positioned to stay in contact with the skin tissue substantially adjacent to a second ear of the user via a second housing fastened to the second leg of the eyewear.

In some embodiments, the method further includes displaying the physiological measurement data on an external device.

In some embodiments, the first and second sensor arrays include bioimpedance sensors and the physiological measurement data are body fluid status information of the user.

In some embodiments, the method further includes detecting environmental conditions in the vicinity of the user with an environmental sensor.

BRIEF DESCRIPTION OF THE FIGURES

The foregoing is a summary, and thus, necessarily limited in detail. The above-mentioned aspects, as well as other aspects, features, and advantages of the present technology are described below in connection with various embodiments, with reference made to the accompanying drawings.

Figure 1:
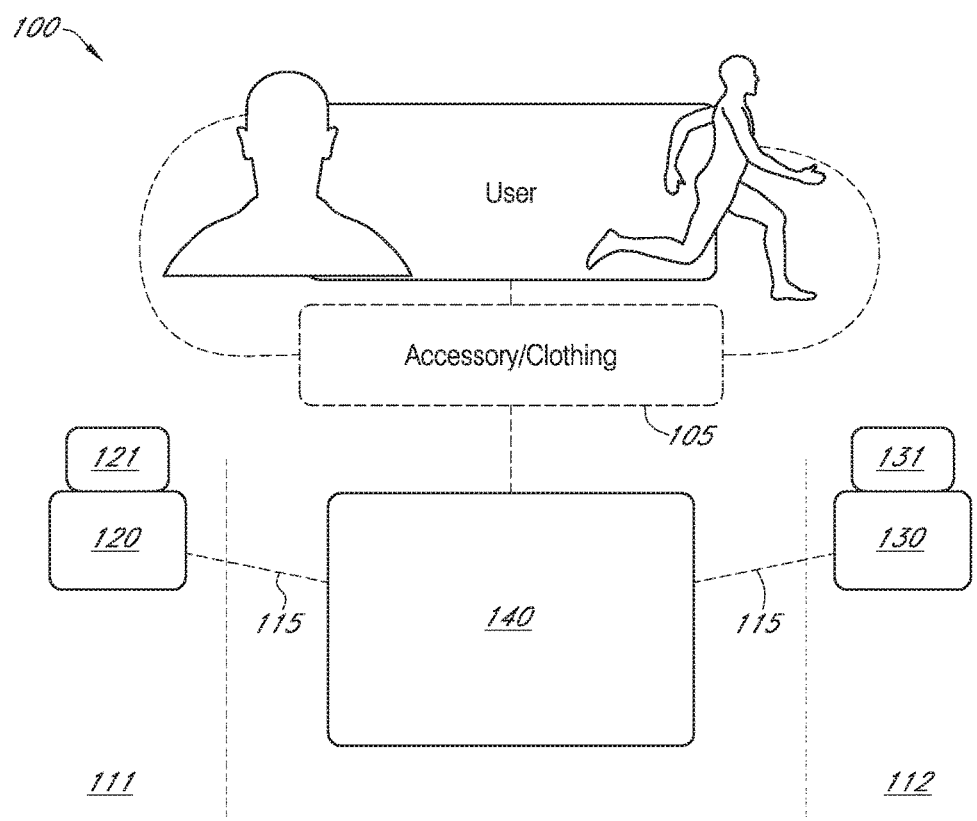
FIG. 1 illustrates a schematic block diagram of one embodiment of a system for detecting and analyzing biosignals.

The illustrated embodiments are merely examples and are not intended to limit the disclosure. The schematics are drawn to illustrate features and concepts and are not necessarily drawn to scale.

DETAILED DESCRIPTION

The above mentioned aspects, as well as other aspects, features, and advantages of the present technology will now be described in connection with various embodiments. The inclusion of the following embodiments is not intended to limit the disclosure to these embodiments, but rather to enable any person skilled in the art to make and use the contemplated invention(s). Other embodiments may be utilized and modifications may be made without departing from the spirit or scope of the subject matter presented herein. Aspects of the disclosure, as described and illustrated herein, can be arranged, combined, modified, and designed in a variety of different formulations, all of which are explicitly contemplated and form part of this disclosure.

Described herein are systems and methods for measuring and detecting one or more biosignals of a user, for example to determine a health condition of the user.

As described herein, a "user" refers to any individual or species that can wear a head-mounted accessory. Non-limiting examples of users include: a person wearing glasses, a person wearing sunglasses, a person wearing goggles, a person wearing Google Glass® or similar wearable device, a person wearing a headband, a person wearing a hat, a patient, an athlete, a jogger, a swimmer, an elderly person, a person with a long-term health condition, a person released from the hospital, a person admitted to hospital, or any other individual.

As described herein, a "head-mounted accessory" refers to any system or device that is stably and/or securely worn on a head region of a user. Non-limiting examples of head-mounted accessories include: glasses, sunglasses, bifocals, goggles, virtual reality headgear, hats, headbands, masks, Google Glass® or equivalent devices, and earmuffs.

As described herein, a "biosignal" refers to any biological signal detected or measured by the system. Non-limiting examples of biosignals include: bioimpedance signals, temperature signals, pulse oximetry signals, blood flow, blood pressure, heart rate, heart rate variability, electrocardiography signals, electromyography signals, electroencephalography signals, galvanic skin responses, magnetoencephalography impedance signals, acoustic signals, respiration signals, positional signals, caloric intake signals, and hydration signals.

As described herein, "communicatively coupled" refers to communication between two or more system components via a wired or wireless connection. Non-limiting examples of wireless communication include: Bluetooth, low energy Bluetooth, near-field communication, Infrared, WLAN, or other RF technology. Non-limiting examples of wired communication include: IEEE 1394, Thunderbolt, Lightning, DVI, HDMI, Serial, Universal Serial Bus, Parallel, Ethernet, Coaxial, VGA, or PS/2.

Systems

As shown in FIG. 1, one embodiment of a system 100 for detecting and measuring biosignals of a user includes: a first end region 111, a second end region 112, and an intermediate region 140; a first sensor array 120 proximal (e.g., positioned on, embedded within, attached to) the first end region 111; a second sensor array 130 proximal (e.g., positioned on, embedded within, or attached to) the second end region 112; and a coupling element 115 to couple the intermediate region 140 to the first end region 111 and the second end region 112. The system 100 functions to measure and/or detect one or more biosignals of a user wearing the system. For example, the system may function to sense an impedance of current through a linear distance of tissue that separates the first sensor array 120 from the second sensor array 130 to generate metrics of ionic fluid content within the user. The biosignals may be measured using the system substantially continuously and in real time. Alternatively, the user's biosignals may be measured intermittently and/or monitored in real time or non-real time. The system 100 is configured for use in the field of digital health and may be used in any suitable related field, for example, veterinary medicine, sports medicine, or other health or wellness field.

The system 100 functions to couple to clothing or an accessory of a user, in order to detect a set of biosignals from the user. Reliable biosignal measurement and interpretation requires consistent positioning (e.g., location, distance between sensors, etc.) of the sensors over time, particularly in bioimpedance applications. The systems described herein is particularly suited for such applications. The system 100 may couple to the user in a consistent manner, by way of the clothing or accessory, in order to detect biosignals of the user reliably over time (e.g., from one or more precise locations of the user in a repeatable manner). As such, passive and reliable signal measurement quality can be enabled by the system 100. In variations wherein the system 100 is configured to couple to clothing or an accessory, the system 100 is configured to couple to a head-mounted accessory, a piece of head-mounted clothing, or a piece of clothing or accessory worn by the user, in order to detect biosignals from a head region of the user. In non-limiting examples, the system 100 may couple to a user's eyeglasses, sunglasses, or bifocals, as shown in FIGS. 6A-10, in order to detect biosignals from one or more skin regions proximal the user's head or ears (e.g., an area posterior the ear (FIGS. 7A-7B), an area proximal the ear, a superior region of the ear (FIGS. 6A-6B), etc.) in a reliable manner. In one non-limiting example, the user may be of a demographic that uses eyeglasses regularly and/or substantially ubiquitously (e.g., an elderly demographic); however, the user can be of any other suitable demographic.

Figure 5:
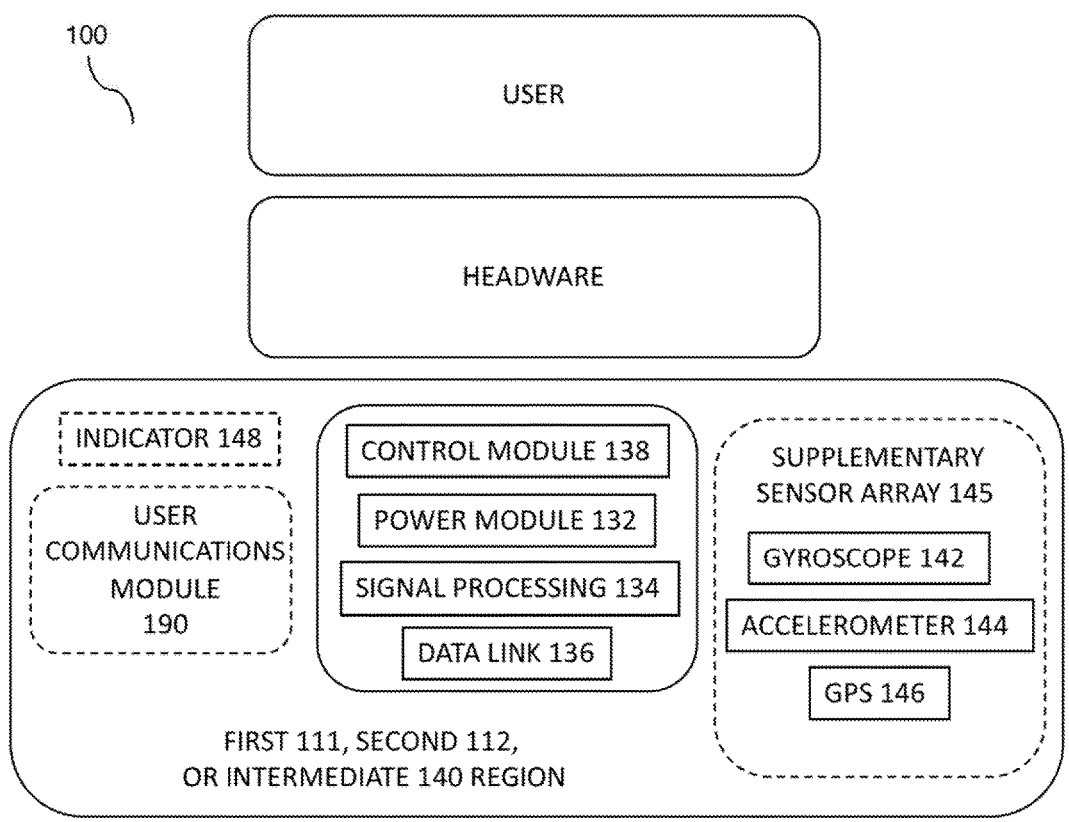
FIG. 5 illustrates a schematic block diagram of one embodiment of a system for detecting and analyzing biosignals.
Figure 6A:
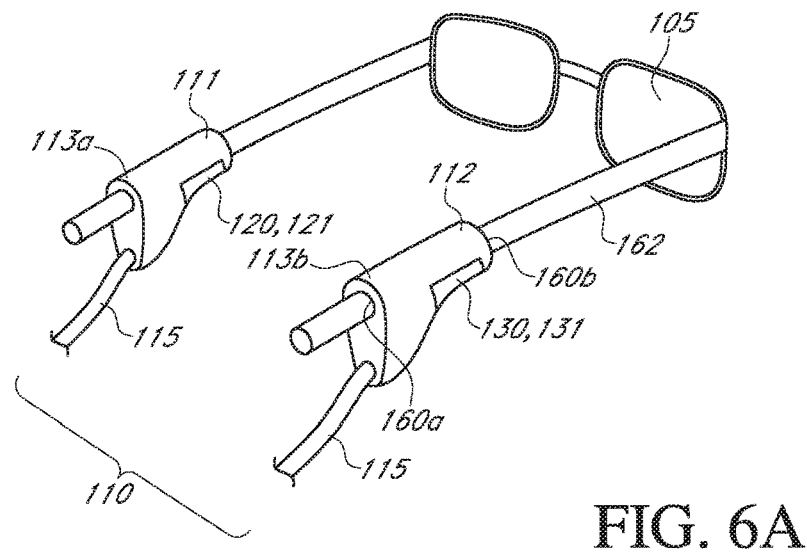
FIG. 6A illustrates a partial perspective view of one embodiment of a system for detecting and analyzing biosignals.
Figure 6B:
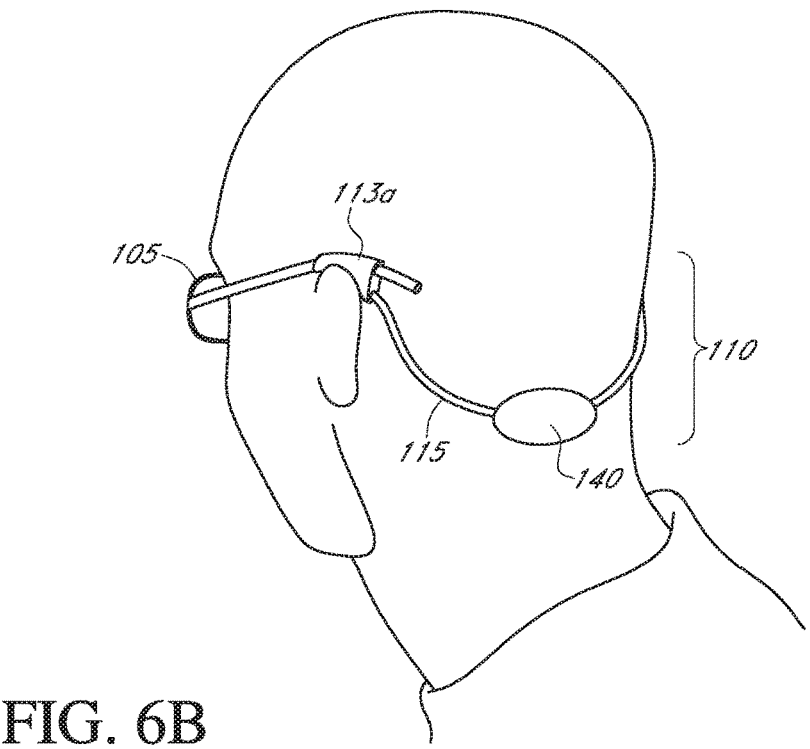
FIG. 6B illustrates a rear view of one embodiment of a system for detecting and analyzing biosignals worn by a user.
Figure 7A:
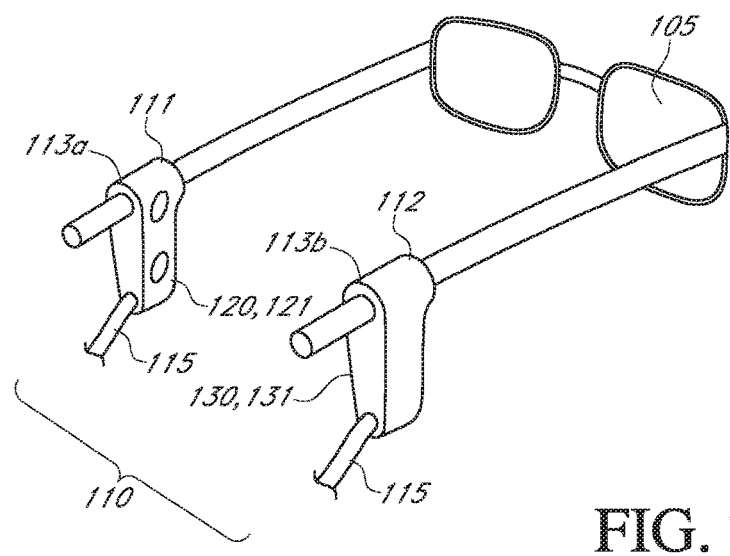
FIG. 7A illustrates a partial perspective view one embodiment of a system for detecting and analyzing biosignals.
Figure 7B:
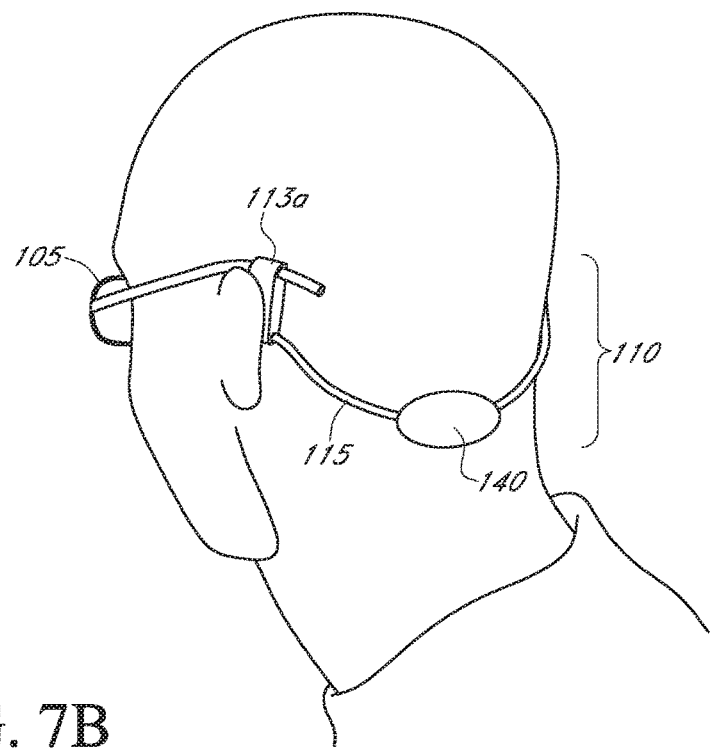
FIG. 7B illustrates a rear view of one embodiment of a system for detecting and analyzing biosignals worn by a user.

In some embodiments, the system 100 is configured to be worn by the user outside of a clinical (e.g., hospital) or research (e.g., laboratory) setting, such that the user can be in a natural, more comfortable environment while using the system 100. Alternatively, in some embodiments, the system 100 can be substantially non-portable, non-wearable, and/or intended for use in a clinical or research setting. Additionally, the system 100 may be unobtrusive and may not inhibit mobility of the user, such that biosignal detection can occur as the user performs normal or routine activities (e.g., walking, exercising, working, etc.) in his/her daily life. Furthermore, components of the system 100 can be reusable or disposable, or the entire system 100 can be configured to be disposable in order to provide a low maintenance system for the user. Additionally, some variations of the system 100 can additionally function to prevent a user from misplacing an accessory or article of clothing to which a portion of the system 100 is coupled. For example, as shown in FIG. 5, the system may include one or more tactile (e.g., vibration), audible (e.g., beeping, buzzing, dinging, music, etc.), and/or visual (e.g., LED, OLED, colored light, etc.) location indicators 148 to help a user locate the system when it is unattached to the head-mounted accessory.

In embodiments of the system comprising the head-mounted accessory, the head-mounted accessory may include a user input element, for example a button or toggle switch, to activate a location indicator 148 on a first end region 111, second end region 112, intermediate region 140, coupling element 115, and/or attachment element 113*a*, 113*b* to locate the system.

Figure 2:
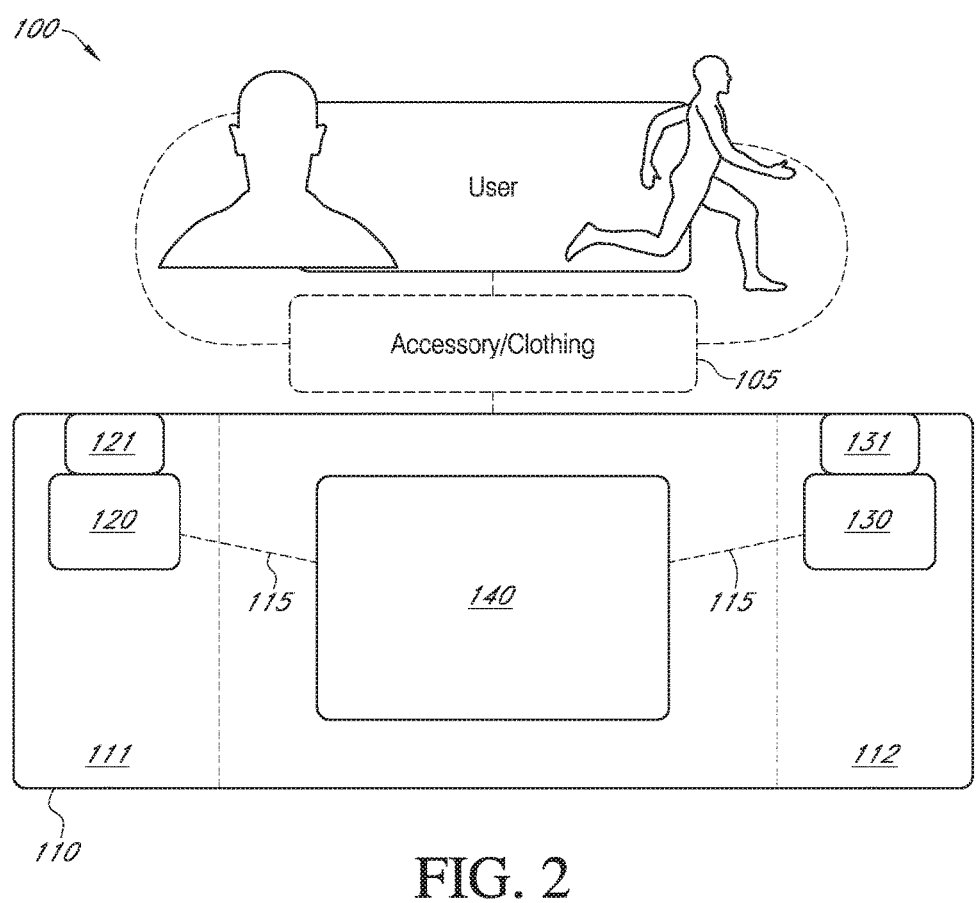
FIG. 2 illustrates a schematic block diagram of one embodiment of a system for detecting and analyzing biosignals.

In some embodiments, as shown in FIG. 2, a system for biosignal detection and measurement optionally includes a housing 110 to house, store, or combine the first end region 111, the second end region 112, and the intermediate region 140, and/or to couple the system to an accessory worn by a user. The housing 110 functions to house and/or protect components of the system 100 in providing a sensor-user interface. In some embodiments, the first end region 111, the second end region 112, and intermediate region 140 are all contained within the housing. For example, the housing 110 may fully encapsulate the components of the system while allowing the first sensor array 120 and second sensor array 130 to continue contacting a skin surface of the user and measuring biosignals of a user. Alternatively, in some embodiments, one or more regions may be positioned within a separate housing or outside of the housing. The housing 110 may further function to position the first sensor array 120 and the second sensor array 130 proximal to regions of the user for biosignal detection in a consistent manner. Further, the housing 110 may facilitate coupling of the first sensor array 120 and the second sensor array 130 to the intermediate region 140 by way of a coupling element 115, as described in further detail elsewhere herein. The housing 110 can additionally function to provide the system 100 to a user in an aesthetic and/or wearable form factor, such that the user is comfortable in wearing the system 100. The housing 110 or the first 111 and second 112 end regions are configured to couple to an accessory or clothing of a user, by way of an attachment element 113*a*, 113*b* as described in further detail elsewhere herein, in order to consistently and repeatedly place the first sensor array 120 and the second sensor array 130 on the user to detect a set of biosignals from the user.

The housing 110 may be flexible in order to enhance user comfort. However, the housing 110 can alternatively be rigid. Furthermore, the housing 110 may be water-resistant or waterproof, such that washing of the housing 110 does not damage the housing 110. As such, the housing 110 may comprise a plastic material, but can alternatively be composed of any other suitable materials, such as polymer, rubber, ceramic, and similar materials.

The material of the housing 110 proximal the first 111 and second 112 end regions may be of a fixed length and provide a cavity of fixed size for each of the temple ends. In one non-limiting example, this material may be cotton, but could be any other suitable material. In another embodiment, the material of the housing 110 may be elastic and form a deformable cavity of variable size for each of the temple ends. In such embodiments, this elastic material may be silicone, but alternatively could be any other suitable material. In some embodiments, the housing 110 may comprise a material that couples to the temple ends via an adhesive, and thus does not require material to surround the temple ends. Alternatively, the housing 110 may comprise any suitable material that functions to couple the sensor arrays 120, 130 to the temple ends of the head-mounted accessory 105, and may take any shape or form such that the design of the housing 110 does not inhibit the daily activities of the user, nor cause discomfort to the user. In one variation, the housing 110 may be completely integrated into the accessory 105, obviating the need for any additional materials.

In some embodiments, as shown in FIGS. 1-10, a system for measuring and detecting biosignals includes a first end region 111 and a second end region 112. The first 111 and second 112 end regions position the first 120 and second 130 sensory arrays on a skin surface of the user, which enables biosignal detection of the user, from multiple sensor arrays. As such, multiple sensor arrays can provide biosignal detection from multiple regions of the user, for instance, in detecting biosignals from contralateral regions of the user (e.g., in detecting bioimpedance), ipsilateral regions of the user, or one region of the user. Additionally or alternatively, the intermediate region 140 of the system may include a third sensor array or supplementary sensor array 145 between the first end region 111 and the second end region 112, in order to provide a sensor-user interface between the first end region 111 and the second end region 112. As such, sensor readings can be obtained from the back of the neck of the user and/or proximal the ears of the user. In some embodiments, the coupling element 115 and/or housing 110 can provide additional sensor array locations along its length, for example at the base of the skull of the user.

As shown in FIGS. 6A, 7A, 8A, 9-10, the first sensor array 120 includes a first electrode 121 proximal (e.g., positioned on, embedded within, attached to) the first end region 111 and the second sensor array 130 includes a second electrode 131 proximal (e.g., positioned on, embedded within, attached to) the second end region 112. The first 120 and second 130 sensor arrays function to directly detect biosignals from a user, wherein each sensor of each sensor array is configured to provide at least one channel for signal detection. For example, the first sensor array 120 and the second sensor array 130 may function to measure an impedance of a current flowing through a volume of tissue (e.g., a head region), and may function to cooperatively detect ionic fluid content within the user based on one or more changes in impedance on an hourly, daily, weekly, monthly, or yearly basis (i.e., for an extended period of time). The first sensor array 120 may be situated at the first end region 111 and the second sensor array 130 at the second end region 112, but can additionally or alternatively be situated at any other suitable region(s) along the housing 110 or coupling element 115. In some embodiments, the system includes at least two sensors or sensor arrays positioned a fixed distance from one another. For example, the distance may comprise the distance between two ears or ear regions of a user.

Each sensor or sensor array of the system is configured to be positioned on a skin surface or region of a user. In some embodiments, each sensor or sensor array is configured to be positioned proximal to an ear or ear region of a user. Non-limiting examples of ear regions include: an area posterior the ear (FIGS. 7A, 8A), an area proximal a superior region of the ear (FIG. 6A), an area below the ear, an area in front of the ear, and an area in the ear. After coupling, the first and second sensor arrays 120, 130, in some embodiments, are positioned contralateral to one another on opposite sides of the head of the user, spaced by a linear distance not to exceed one foot. The contact of each of the sensor arrays 120, 130 with the skin of the user forms a sensor-user interface that is substantially fixed, such that robust contact between the user and the sensor arrays 120, 130 minimizes noise of signal recording due to movement of the sensor arrays 120, 130 against the skin. The sensor-user interface may be located where the sensor arrays 120, 130 couple to the temple end or temple region of the head-mounted accessory 105 and make contact with the user near a region proximal the ear. In some embodiments, the region proximal the ear includes one or more of: at or proximal the pinnae, at or proximal the temple, at or proximal the mastoid process, and/or any other region surrounding or proximal the ear. However, in some embodiments, the location of the sensor-user interfaces can alternatively be defined in any other suitable manner. In one embodiment, the sensor arrays 120, 130 are positioned where each of the temple ends contacts the skin on the top of each pinnae where the pinnae make contact with the head, such that the electrodes 121, 131 make direct contact with the skin. In another non-limiting embodiment, the sensor arrays 120, 130 are positioned where the medial side of each of the temple ends faces the skin, posterior to where each of the pinnae makes contact with the head, such that the electrodes 121, 131 make direct contact with the skin. Alternatively, the sensor-user interfaces can be non-fixed, and the system 100 can be configured to distinguish and compensate for motion of the arrays relative to the user's body.

In some embodiments, sensor arrays 120, 130 contact a skin region proximal to a user's skeletal system (e.g., external acoustic meatus, temporal bone, occipital bone, cervical vertebrae, etc.), a user's nervous system, a user's circulatory system, and/or user's musculoskeletal system. In some embodiments, one or more sensors or sensor arrays are configured to detect signals generated at any one or more of the posterior auricular artery, the occipital artery, the vertebral artery, the internal jugular vein, internal carotid artery, and any other suitable blood vessel. In some embodiments, one or more sensors or sensor modules are configured to detect signals generated at nerves (e.g., cranial nerves I-XII, auricular nerve, greater and lesser occipital nerve, branches of dorsal rami of C4, C5, and C6 spinal nerves, suboccipital nerve, etc.) and/or brain regions (e.g., temporal lobe, occipital lobe, etc.) of the user. In some embodiments, one or more sensors or sensor arrays are configured to detect signals generated at any one or more of: the temporalis muscle, the extraocular muscles, the sternocleidomastoid muscle, the trapezius muscle, the splenius capitis muscle, the semispinalis capitis muscle, the semispinalis cervicis muscle, the splenius cervicis muscle, the longissimus capitis muscle, the splenius capitis muscle, the obliquus capitis superior muscle, the semispinalis capitis muscle, the rectus capitis posterior major muscle, the rectus capitis posterior minor muscle, and any other suitable head/neck region muscle of the user.

The first 120 and second 130 sensor arrays are configured to enable detection of one or more of: bioimpedance signals, temperature signals, pulse oximetry signals, blood flow (e.g., cerebral blood flow), blood pressure, heart rate, heart rate variability, electrocardiography (ECG), electroencephalography (EEG) signals, electromyography signals, galvanic skin response (GSR signals), magnetoencephalography (MEG) impedance signals, acoustic signals, respiration signals (e.g., respiration rate, depth of breath, thoracic variations, inspiratory flow characteristics, expiratory flow characteristics, etc.), positional or location signals, caloric intake, hydration status (e.g., dehydrated, hyponatremic), and/or any other signal obtained from or related to biological tissue or biological processes of the user, as well as the environment of the user.

In one non-limiting example, positional information can, for example, provide information to a healthcare provider, an emergency response team, or another contact of the user in the event that an adverse health condition (e.g., a seizure) is detected using the system 100. In another non-limiting example, signals from the sensors can facilitate detection of a mental state (e.g., by vocal parameters detected at an acoustic sensor, by detected EEG signals, etc.), for example if the user is experiencing a stroke or a Multiple Sclerosis flare up. In another non-limiting example, detecting a hydration status (e.g., using bioimpedance) of the user may detect kidney failure, dehydration, hyponatremia, fluid overload, pleural effusion, etc. In another non-limiting example, detecting blood flow (e.g., using photoplethysmography) of the user may detect a stroke, blood clot, heart failure, etc. Any one or more of the above signals can be detected using the first electrode 121 and/or second electrode 131; however, the first sensor array 120 and/or second sensor array 130 can additionally or alternatively include any number of additional electrodes or sensors configured to facilitate different types of biosignal detection.

In some embodiments, the sensor arrays 120, 130 may be configured to detect signals in response to specified triggers such as a movement of the sensor array 120, 130 or pressure applied against the sensor array 120, 130. In one non-limiting example, the sensor arrays 120, 130 may automatically begin detection of biosignals after recognizing an applied pressure from the associated first 111 and second 112 end regions that receive the generated pressure by a worn head-mounted accessory. In other non-limiting examples, the sensor arrays 120, 130 may automatically begin detection of biosignals when it comes into contact with the user's skin surface or when it recognizes the movement of a coupled pair of glasses that is being placed onto a user (e.g., FIGS. 9-10). Alternatively, the sensor arrays 120, 130 may be activated by a user (e.g., through voice, a button, remote device). The sensor arrays 120, 130 may, in some embodiments, be configured to conserve electrical power by performing detection at a rate that varies depending on the remaining electrical power or on additional information regarding the biosignals, characteristics, health conditions, and/or activities.

Figure 9:
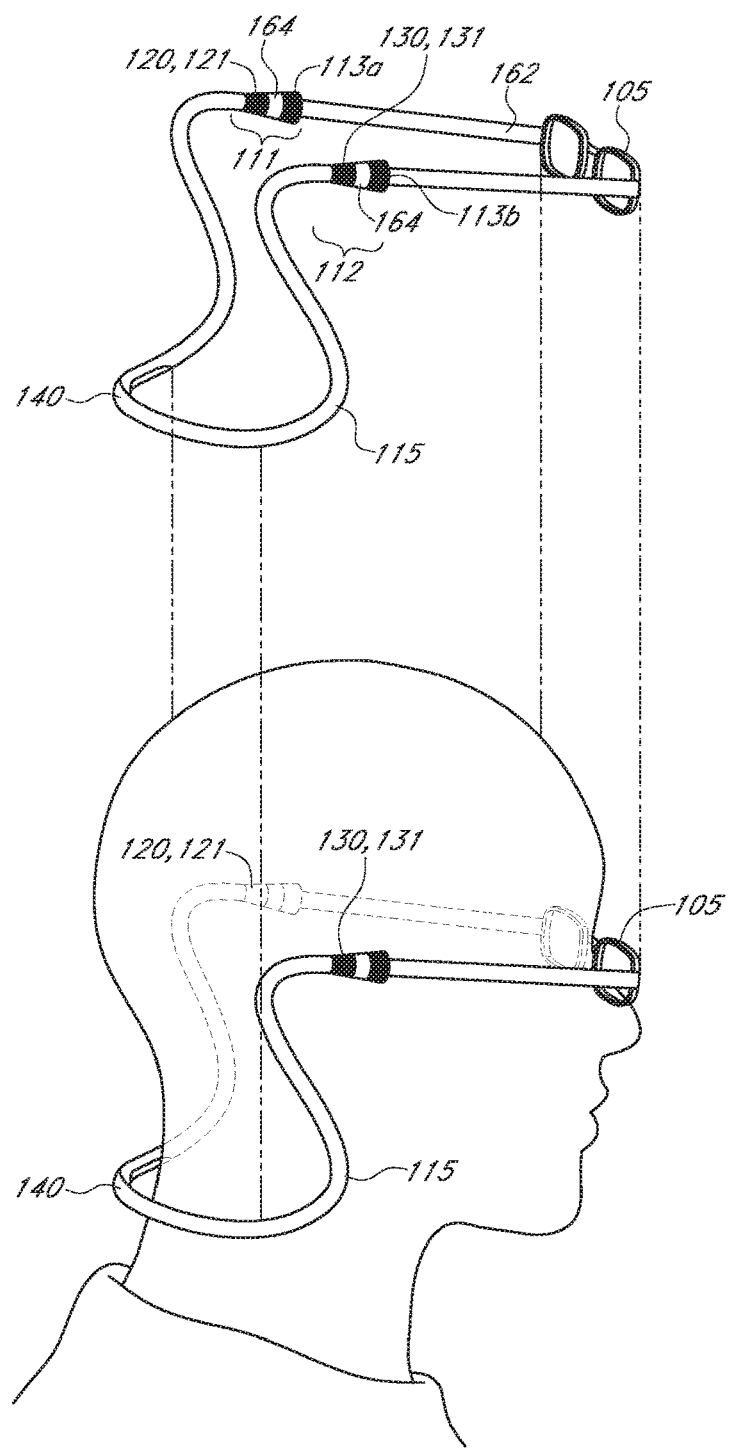
FIG. 9 illustrates a side view of one embodiment of a system for detecting and analyzing biosignals worn by a user.
Figure 10:
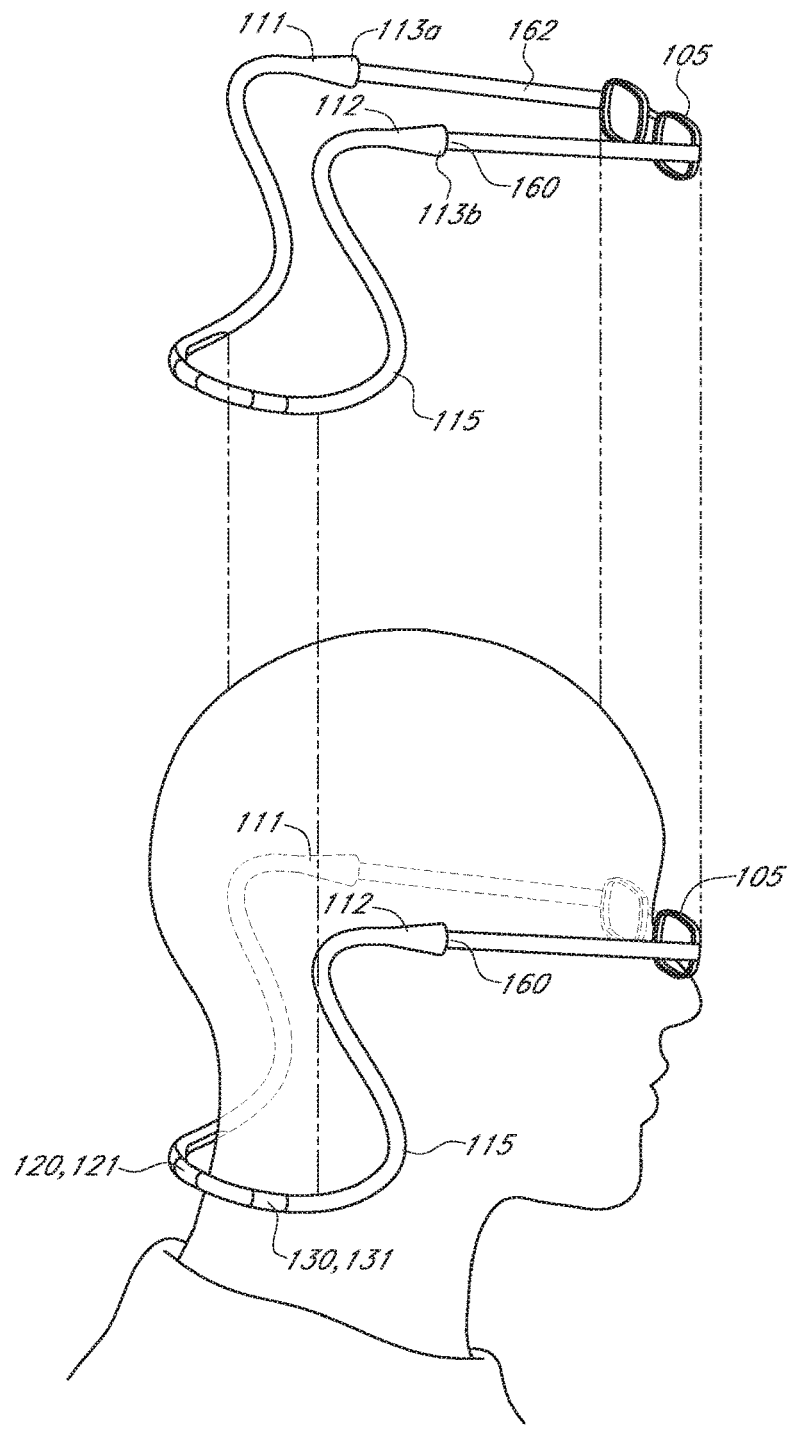
FIG. 10 illustrates a side view of one embodiment of a system for detecting and analyzing biosignals worn by a user.

In some embodiments, as shown in FIGS. 9-10, the sensor arrays 120, 130 are positioned at contralateral locations of the user, with a consistent or fixed distance (e.g., distance between ears of a user) between a first electrode 121 and a second electrode 131, for example for reliable bioimpedance applications. As such, the system enables reliable sensor measurements by way of consistent sensor placement. Current systems refrain from measuring biosignals on or near the head region due to a low signal-to-noise ratio. However, the systems described in the present disclosure enable reliable sensor measurements since the sensors are positioned substantially in the same position for extended periods of time (i.e., an entire time a user is wearing his/her eyewear) because the system is coupled to an eyewear of the user. For example, a user may wear his/her eyewear for sixteen hours, fourteen hours, twelve hours, ten hours, eight hours, or any length of time. Extended periods of measurement and consistent sensor placement improve the system's ability to differentiate true signals from background noise.

While the system 100 includes at least the first sensor array 120 and the second sensor array 130, the system 100 can alternatively include any other suitable number of sensor arrays positioned at any suitable location relative to the housing 110 (e.g., at an intermediate region of the housing) and/or along the length of the coupling element 115. For example, as shown in FIG. 10, the first 120 and second 130 sensor arrays are positioned along the length of the coupling element 115 of the system as opposed to proximal the first 111 and second 112 end regions of the system. Furthermore, any sensor array can include a module configured to enhance a sense (e.g., sight, sound, taste, smell, touch) or an environment of the user. For example, a portion of a sensor array and/or the first 111 and second 112 end regions may include a hearing aid module configured to enhance hearing of the user, a speaker for projecting audio into an ear of the user, and/or a microphone for receiving vocal sounds or audio from the user or an environment surrounding the user.

Any of the sensor arrays 120, 130 of the system 100 can incorporate a wet electrode (e.g., electrode wettable with saline in order to facilitate signal transduction), a dry electrode (e.g., polymer sensors), and/or any other suitable electrode/sensor for biosignal transduction. The electrodes 121, 131 may be composed of any conductive material or materials that are solid or gel-like, including, but not limited to: metals, conductive polymers, conductive gels or sol-gels, alloys, conductive plastics, semimetals or semiconductors, and the like. Silver chloride electrodes, carbon rubber, copper and gold electrodes are just a few examples of electrode materials. The sensor arrays are preferably non-invasive (i.e., the sensors remain external to the user); however, the sensor arrays can additionally or alternatively be configured to penetrate the body of the user. For example, a sensor array can incorporate a microneedle array configured to penetrate a user's stratum corneum to facilitate signal detection (e.g., at an interstitial fluid of the user).

As shown in FIGS. 6A-10, a system for detecting and measuring biosignals may further include first and second attachment elements 113*a*, 113*b*. Each attachment element 113*a*, 113*b* functions to couple the first end region 111 and the second end region 112 to the accessory 105 (e.g., head-mounted accessory) worn by the user. Each attachment element 113*a*, 113*b* is configured to secure the end regions 111, 112 substantially in place on either side of the head of the user via the pressure of a temple region or temple ends against the head of the user to ensure accurate biosignal measurement by electrodes 121, 131. Coupling the system to an accessory 105 worn by the user ensures consistent, repeatable contact on the same skin location during each measurement session. Furthermore, the system is configured to be easily reversibly coupled from the accessory 105 while still promoting consistent placement of the sensors relative to the user over repeated instances of donning and removing the system. Each attachment element 113 includes any one or more of: an aperture, a sleeve, a clasp, a magnet, an adhesive, a strap, a snap-fit, and any other suitable element that facilitates coupling the first 111 and second 112 end regions to the accessory or clothing in a reversible manner.

In one non-limiting example shown in FIGS. 6A-6B, 7A-7B, 8A-8B, each attachment element 113*a*, 113*b* includes an aperture 160 configured to receive a temple or temple region 162 (i.e., leg) of an eyewear accessory 105. The temple or temple region 162 slides through a first end 160*a* of the attachment element 113*b* and out a second end 160*b* of the attachment element 113*b*. The aperture may include an adjustable diameter. In one embodiment, the diameter of the aperture may be adjusted using an elastic cord circumscribing the aperture. In another embodiment, as shown in FIG. 10, the material circumscribing the aperture 160 may comprise elastic material so that the aperture 160 conforms to the size and/or shape of the accessory 105.

In another non-limiting example shown in FIGS. 9-10, each attachment element 113*a*, 113*b* comprises a sleeve or tube configured to receive a temple end or temple region 162 of the accessory 105. The sleeve or tube may comprise elastic or deformable material, as shown in FIG. 10, such that the sleeve or tube conforms to the temple end or temple region 162 of the accessory 105 to secure the first 11 and second 112 end regions to the accessory 105. In some embodiments, the sleeve or tube may comprise a rotatable or adjustable cuff 164, as shown in FIG. 5, such that the diameter of the sleeve or tube is increased or decreased to conform to a size and/or shape of the temple end or temple region 162 of the accessory 105 to secure the first 111 and second 112 end regions to the accessory 105. In some embodiments, the attachment element 113*a*, 113*b* may irreversibly or fixedly connect or couple the system to the accessory or clothing so that the system and the accessory cannot be separated.

In some embodiments, as shown in FIG. 1-4, 6A-6B, 7A-7B, 9, 10, a system for detecting and measuring biosignals includes a coupling element 115. The coupling element 115 functions to physically and/or electrically couple the first 111 and second 112 end regions to the intermediate region 140. In some variations, at least a portion of the coupling element 115 may be configured to be detached (e.g., reversibly attached and detached), disunited, or otherwise removed from the system 100 in any suitable manner. As such, the coupling element 115 is configured to prevent a choking hazard in variations wherein elements of the system 100 are proximal the user's neck. In these variations, the coupling element 115 can additionally or alternatively enable sensor arrays to remain coupled to the user (e.g., by way of the user's accessory/clothing), while allowing detachment of portions of the coupling element 115, for instance, during charging. In variations of reversible attachment and detachment from the system 100, the coupling element 115 may include portions that provide an electromechanical coupling interface with at least one of the first end region 111 and the second end region 112. In some variations, the coupling element 115 can additionally or alternatively be configured to have an adjustable length (e.g., by stretching, by lengthening, by shortening, etc.) to facilitate proper function and/or user comfort. However, the coupling element 115 and/or any other portion of the system 100 can be configured in any other suitable manner.

In one non-limiting example, as shown in FIGS. 9-10, the coupling element 115 comprises a lanyard form factor including first and second attachment elements 113a, 113b proximal (e.g., attached or coupled to) the first end region 111 and the second end region 112, configured to form sleeves or apertures that couple to the user's eyewear accessory 105. As such, the coupling element 115 includes flexible and/or elastic regions proximal the first end region 111 and the second end region 112 that can be configured to surround and/or grip the one or more regions (e.g., temple end or temple region) of the user's eyewear accessory 105. In some embodiments, the coupling element 115 can alternatively take any suitable form, such as a cable or strap, and can be worn fore or aft of the facial region. The materials used for the coupling element can alternatively range from fibrous blends such as cotton or nylon, to elastomers such as silicone and other plastics, and are preferably selected to enhance the wearability of the system. In some embodiments, the coupling element 115 comprises electrically insulating and/or electrochemically inert materials. In some such embodiments, the coupling element 115 may comprise plastic, rubber, or fabric.

In some embodiments, as shown in FIGS. 1-4, 6B, 7B, 9, and 10, a system for detecting and measuring biosignals includes an intermediate region 140. The intermediate region 140 functions to house one or more system components, for example a processor, memory, antenna, transceiver, etc.

The intermediate region 140 functions to provide regulated power to the system 100, to facilitate detection of biosignals from the user by incorporating signal processing elements interfacing with the first sensor array 120 and the second sensor array 130, to couple to additional sensors for comprehensive collection of data relevant to the user and/or the biosignals being detected, and to enable transmission and/or reception of data by the system 100, for example to or from a computing device 170 and/or service 180 communicatively coupled to the system. As such, as shown in FIG. 5, the intermediate region 140 may include a power module 132, a control module 138, a signal processing module, and a data link 136, to provide inputs and/or outputs to other elements of the system 100 (e.g., the sensor arrays 120, 130).

In some variations, as shown in FIG. 5, the intermediate region 140 can additionally or alternatively include a supplementary sensor array 145 configured to provide additional contextual data that can be used, along with data generated using the first sensor array 120 and the second sensory array 130, to enable a more complete analysis of the biosignals of the user. The intermediate region 140 may include an integrated circuit (IC), which can be a system-on-chip IC, but can additionally or alternatively include any other suitable type of IC. The intermediate region 140 is configured to be physically and/or electrically coupled to the first sensor array 120 and the second sensor array 130, for example, by way of a coupling element 115. In one variation, the power module 132, control module 138, signal processing module (e.g., processor, memory, etc. as described elsewhere herein), and/or data link 136 are embedded at a recessed region or cavity of the intermediate region 140, with leads coupled to the first and the second sensor arrays 120, 130. In another variation, the power module 132, control module 138, signal processing module (e.g., processor, memory, etc. as described elsewhere herein), and/or data link 136 are coupled to an external portion of the housing 110, with electric coupling to each of the first and the second sensor arrays 120, 130. In still another variation, the power module 132, control module 138, signal processing module (e.g., processor, memory, etc. as described elsewhere herein), and/or data link 136 can include miniaturized electronics that can be embedded in the intermediate region 140, first 111 and/or second 112 end regions, and/or in the housing 110 in the form of a miniaturized module (e.g., cable, cord). However, the power module 132, control module 138, signal processing module 134 (e.g., processor, memory, etc. as described elsewhere herein), and/or data link 136 can be coupled to the housing 110 and/or the sensor arrays 120, 130 in any other suitable manner.

As shown in FIG. 5, the power module 132 functions to store and distribute energy in order to power the system 100. As such the power module 132 comprises an energy storage element, and can be configured to couple to a charging module 150, as described in further detail elsewhere herein. The energy storage element may be a battery coupled to voltage regulation and power distribution circuitry and, in some embodiments, is rechargeable. However, some variations of the system 100 may omit a rechargeable energy storage element and charging module 150. In variations wherein the energy storage element is rechargeable, the energy storage element may comprise a lithium-ion polymer battery but can alternatively include any other suitable rechargeable battery (e.g., nickel-cadmium, metal halide, nickel metal hydride, or lithium-ion). The battery (or other suitable energy storage element) may be configured to charge or recharge by a wireless connection (e.g., by inductive charging using a charging module 150), but can additionally or alternatively be configured to charge or recharge by a wired connection (e.g., stereo connection, universal serial bus connection, custom connection) or by any other suitable means (e.g., by energy harvesting, by solar charging, etc.). In variations wherein the energy storage element is a non-rechargeable battery, the battery may comprise a lithium battery, an alkaline battery, or other non-rechargeable battery that can be replaceable to enhance modularity in the system 100. A non-rechargeable battery can further facilitate applications in which at least a portion of the system 100 is disposable.

As shown in FIG. 5, the control module 138 of some embodiments is a programmable module, is coupled to the power module 132, and functions to control the system 100. The control module 138 comprises a processor (e.g., a general purpose microprocessor, a digital signal processor (DSP), a field programmable gate array (FPGA), an application specific integrated circuit (ASIC), other programmable logic device or array, other discrete computer-executable components, etc.). In some embodiments, the processor includes a combination of computing devices (e.g., DSP and general purpose microprocessor), one or more processors in conjunction with a DSP core, or any other suitable combination to perform the methods described elsewhere herein.

In some embodiments, the processor is coupled, via one or more buses, to the memory in order to read information from, and optionally write information to, the memory. The memory may be any suitable computer-readable medium that stores computer-readable instructions for execution by a processor. For example, the computer-readable medium may include one or more of RAM, ROM, flash memory, EEPROM, a hard disk drive, a solid state drive, or any other suitable device. In some embodiments, the computer-readable instructions include software stored in a non-transitory format. The software may be programmed into the memory or downloaded as an application onto the memory. The software may include instructions for running an operating system and/or one or more programs or applications. When executed by the processor, the programs or applications may cause the processor to perform a method of detecting, recording, processing, and/or analyzing biosignals. Some such methods are described in more detail elsewhere herein.

In some embodiments, the processor is configured to control powering of the system 100, handling of signals received by the system 100, distribution of power within the system 100, and/or any other suitable function of the system 100. The control module 138 may facilitate at least a portion of a method for detecting and analyzing biosignals of the user as described elsewhere herein, but can additionally or alternatively be configured to facilitate any other suitable method. In some variations, the control module 138 can be preconfigured to perform a given method, with the system 100 configured such that the processor cannot be reconfigured to perform a method different from or modified from the given method. However, in other variations of the system 100, the processor can be reconfigurable to perform different methods.

In some embodiments, based on the detected biosignals, the processor may be configured to generate a medically relevant metric (e.g., current heart condition, mental health) that is interpretable without further analysis by a trained professional (e.g., doctor, researcher, caretaker). Alternatively, the processor may generate medically relevant metrics that trained professionals (e.g., doctor, researcher, caretaker) can use to diagnose health conditions (e.g., disease, physiological state). In some embodiments, the processor is configured to associate recorded biosignals (e.g., bioimpedance, heart rate) with user data (e.g., walking, standing up, location, etc.) captured by the supplementary sensor array 145 (e.g., gyroscope, accelerometer, GPS, etc.). In some embodiments, the processor is configured to associate user data (e.g., walking, standing up, location, etc.) with biological characteristics (e.g., fluid status, heart rate variability, etc.) derived from an analysis of detected biosignals (e.g. bioimpedance, heart rate, etc.). In some embodiments, the processor is further configured to generate a recommendation for the user to perform a certain action (e.g., sit down to reduce heart activity, drink water, contact a doctor's office, etc.) in response to a diagnosed or assessed health condition (e.g., high risk of cardiac arrest, low fluid status, etc.). In some such embodiments, a user may be notified of a medically relevant metric or recommendation through a remote device (e.g., application on mobile computing device, website, etc.) associated with the system 100. Alternatively, a user may be notified through a user communications module 190, as described elsewhere herein.

As shown in FIG. 5, the signal processing module 134 of some embodiments comprises an amplifier, a filter, a clock, a function generator, a digital-to-analog converter (DAC), and an analog-to-digital converter (ADC), and can additionally comprise a multiplexer configured to multiplex signals from multiple sensor channels of the first sensor array 120 and the second sensory array 130. As such, the signal processing module 134 functions to process detected and received biosignals from the set of sensors, in order to facilitate further processing and/or signal analysis. The signal processing module 134 may be coupled to the first sensor array 120 and the second sensor array 130 and to the control module 138, in order to facilitate handling of detected biosignals and signal processing. In variations wherein the signal processing module 134 includes a multiplexer, the amplifier can be placed after the multiplexer in order to amplify a single output line. Additionally or alternatively, the signal processing module 134 can include one or more amplifiers placed prior to a multiplexer, in order to amplify input lines to the multiplexer. The ADC can be characterized by any suitable number of bits, and in a specific example, is characterized by 16-bits. The ADC can also comprise an internal voltage reference to facilitate signal processing. The intermediate region 140 may comprise any suitable number of ADCs for conversion of analog signals (e.g., from multiple channels) into digital quantizations. Furthermore, the signal processing module 134 can incorporate one or more filters configured to filter transient signals (e.g., resulting from multiplexing, resulting from noise, or resulting from any other factor).

Figure 3:
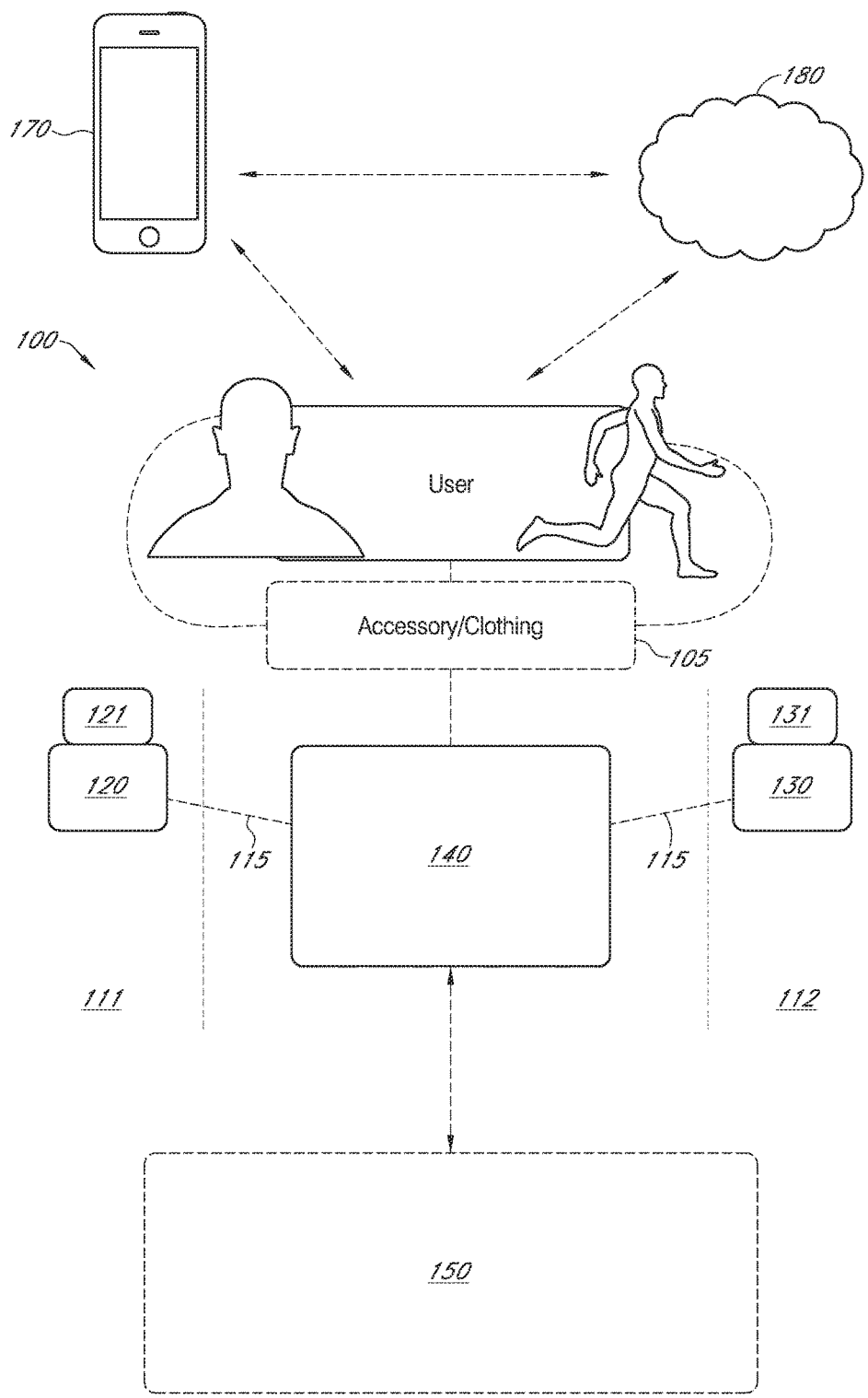
FIG. 3 illustrates a schematic block diagram of one embodiment of a system for detecting and analyzing biosignals.

As shown in FIGS. 3 and 5, the data link 136 of some embodiments, is coupled to the control module 138, and functions to transmit an output of at least one component of the system to a mobile device 170 (e.g., laptop computer, tablet, smartphone, health tracking device, personal digital assistant (PDA), a wearable device (e.g., Google Glass®, FitBit®, Pebble®, Apple Watch®, etc.), netbook, notebook, etc.), to another computing device (e.g., desktop computer, workstation, health tracking device, etc.), server 180 (e.g., cloud, a virtual server, a database server, an application server, an internet server, other remote server), and/or to any other suitable storage/processing system. In some embodiments, the data link 136 is a wireless interface (e.g., via Bluetooth, low energy Bluetooth, near-field communication, Infrared, WLAN, or other RF technology); however, the data link 136 can alternatively be a wired connection (e.g., IEEE 1394, Thunderbolt, Lightning, DVI, HDMI, Serial, Universal Serial Bus, Parallel, Ethernet, Coaxial, VGA, PS/2). In some embodiments, there is bidirectional communication between the data link 136 and the computing device 170, the data link 136 and the server 180, and the computing device 170 and the server 180.

In some embodiments, the data link 136 may include a Bluetooth module that interfaces with a second Bluetooth module included in the computing device or a system component (e.g., server), wherein data or signals are transmitted by the data link 136 to/from the computing device or system component over Bluetooth communications. In some embodiments, the data link 136 may alternatively implement other types of wireless communications (e.g., 3G, 4G, infrared, WLAN, other radiofrequency technology, near field communication (NFC)). In some embodiments, data and/or signals are encrypted before being transmitted by the data link 136. For example, cryptographic protocols such as Diffie-Hellman key exchange, Wireless Transport Layer Security (WTLS), or any other suitable type of protocol may be used. The data encryption may also comply with standards such as the Data Encryption Standard (DES), Triple Data Encryption Standard (3-DES), or Advanced Encryption Standard (AES).

In some embodiments, the data link 136 includes an antenna or transceiver. In some embodiments, the antenna includes one or both of a receiver and a transmitter. The receiver receives and demodulates data received over a communication network. The transmitter prepares data according to one or more network standards and transmits data over a communication network. In some embodiments, a transceiver antenna acts as both a receiver and a transmitter for bi-directional wireless communication. As an addition or alternative to the antenna, in some embodiments, a databus is provided so that data can be sent from, or received by, one or more sensors or sensor arrays via a wired connection.

In some variations, as shown in FIG. 5, the intermediate region 140, the housing 110, the first end region 111, the second end region 112, and/or the coupling element 115 can additionally or alternatively include or be coupled to a supplementary sensor array 145 configured to detect a set of supplementary signals. As shown in FIG. 5, the supplementary sensor array 145 may include at least one of a gyroscope 142, an accelerometer 144, and a global positioning sensor 146, and functions to provide supplementary data relevant to actions being performed by the user as the user is coupled to the system 100. The supplementary sensor array 145 is coupled to the control module 138 to enable detection of orientation, motion (e.g., as a pedometer), and/or position of the system 100 and/or user; however, the supplementary sensor array 145 can be coupled to the user in any other suitable manner (e.g., at a computing device of the user) and/or detect orientation, motion, and/or position of the user in any other suitable manner. In variations wherein the supplementary sensor array 145 comprises a gyroscope 142, the gyroscope 142 functions to detect an orientation of the system 100. The gyroscope 142 can be a 2-axis gyroscope, a 3-axis gyroscope, or any other suitable gyroscope 142 for orientation detection. In variations wherein the supplementary sensor array 145 comprises an accelerometer 144, the accelerometer 144 functions to enable acceleration detection of the user and/or the system 100. The accelerometer 144 can be a single axis accelerometer, a 2-axis accelerometer, or a 3-axis accelerometer. In these variations, the accelerometer 144 and the gyroscope 142 may be configured to measure data associated with determining a user's posture (e.g., standing, slouching, laying down) and a user's activity (e.g., walking, resting, eating, active, inactive). In variations, wherein the supplementary sensor array 145 comprises a global positioning sensor (GPS) 146, the GPS 146 functions to enable location detection or positional information of a user while the system 100 is coupled to the user. The system 100 can, however, comprise any additional or alternative sensing units, and can comprise multiples of a given sensing unit in order to provide sensor redundancy.

The intermediate region 140 can additionally or alternatively comprise any other suitable element or combination of elements for providing regulated or unregulated power to the system 100 and/or controlling elements of the system 100. Furthermore, the intermediate region 140 can additionally or alternatively comprise any other suitable combination of elements for handling biosignal detection, biosignal processing, and/or biosignal transmission, in a manner that provides sufficient sensitivity.

Furthermore, additional sensor arrays can facilitate signal detection from any other suitable physiological system (e.g., auditory system, respiratory system, etc.) of the user, at any other region of the user's body. In such variations, the housing 110 can couple to a headwear accessory or clothing item (e.g., hat, cap, earphones, headpiece, etc.) of the user in order to position the sensor arrays 120, 130 to detect biosignals from other head regions of the user. In still other variations, the housing 110 can couple to any other region of the user or the user's clothing, in order to position sensor arrays 120, 130 to detect any other suitable biosignal of the user in a reliable manner.

Figure 8A:
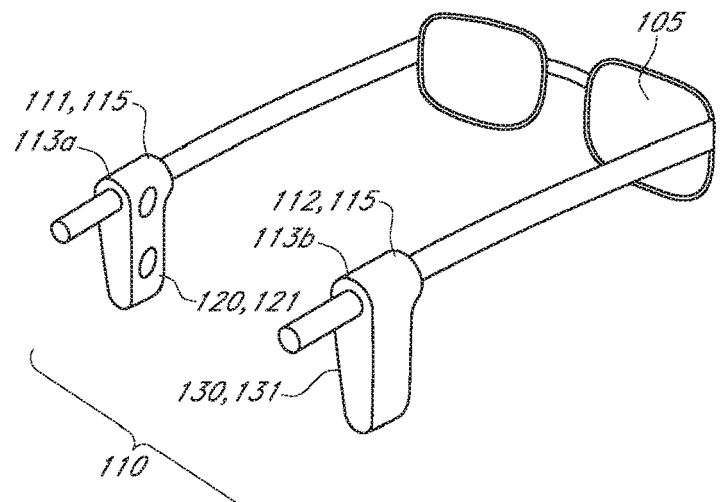
FIG. 8A illustrates a perspective view of one embodiment of a system for detecting and analyzing biosignals.
Figure 8B:
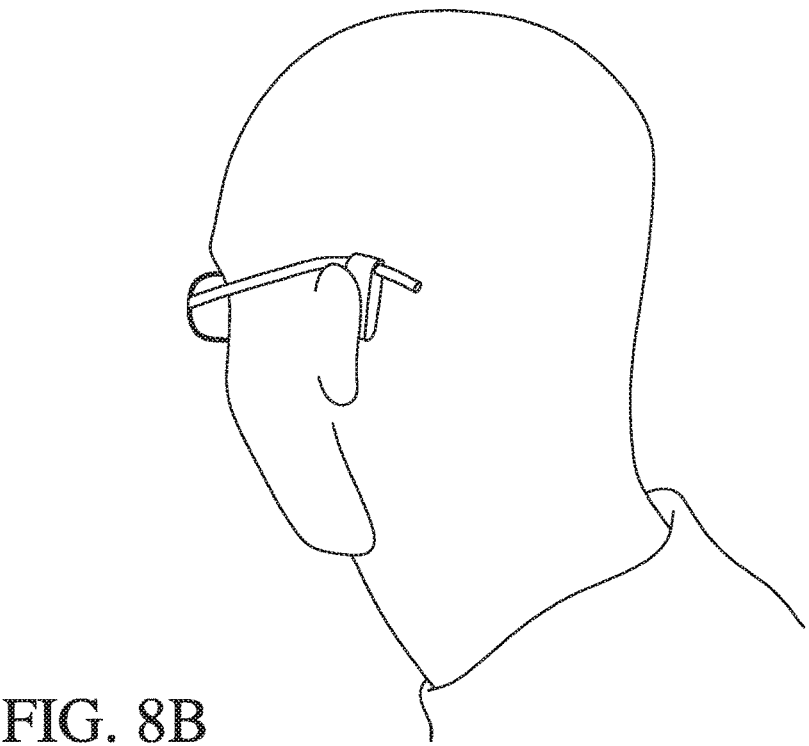
FIG. 8B illustrates a side rear view of one embodiment of a system for detecting and analyzing biosignals worn by a user.

In some embodiments, the first end region 111 and the second region 112 are coupled to the intermediate region 140, as described elsewhere herein. Alternatively, in some embodiments, as shown in FIGS. 8A-8B, the first end region 111 and the second end region 112 are uncoupled from each other. In some such embodiments, the system components (e.g., power module 132, control module 138, signal processing module 134, data link 136, etc.) may reside in the first end region 111, the second end region 112, and/or on a computing device 170 communicatively coupled to the first 111 and/or second 112 end regions.

In some embodiments, all detecting, measuring, and analyzing of biosignals is performed by one region of the system, for example the first end region 111, the second end region 112, or the intermediate region 140. In some such embodiments, the system may only include one region. Alternatively, in some embodiments, one region may include components for detecting and measuring biosignals while one or more other regions process and/or analyze the biosignals.

Returning to FIG. 3, in some embodiments, the system 100 may further include a charging module 150 configured to interface with the intermediate region 140 in order to facilitate charging of the system 100. As such, the charging module 150 functions to charge an energy storage element (e.g., battery) of the intermediate region 140 to enable the system 100 to function properly. The charging module may provide inductive coupling of power between the charging module 150 and the power module 132 of the intermediate region 140, for example, by way of a charging coil coupled to the energy storage element of the intermediate region 140. The charging coil can thus convert energy from an alternating electromagnetic field provided by the charging module into electrical energy to charge the energy storage element without a wired connection. Inductive charging can further allow electrical isolation between an external power supply coupled to the charging module 150 and internal electronics of the intermediate region 140, to facilitate increased patient safety. Inductive charging provided by the charging coil thus also facilitates patient mobility while interacting with the system 100, such that the patient can be extremely mobile while managing his or her health with the system 100.

The charging module 150 may include any suitable form factor, and can be disguised to further decrease awareness that the user is interfacing with the system. Disguising of the charging module 150 can further provide a low-maintenance solution to regular charging of the system 100. In some embodiments, the charging module 150 can comprise a form factor of an eyewear accessory stand, such that placing the system 100, coupled to the user's eyewear accessory, on the eyewear accessory stand facilitates charging of the system 100. In some such embodiments, for example for an elderly user, the form factor of the charging module can facilitate other regular activities of the user (e.g., denture use, medication adherence, etc.), by incorporating storage modules for other items that the user uses regularly (e.g., dentures, medications, etc.). Such incorporation of storage modules can promote usage of the system 100 and maintenance of the system 100 by the user. In another variation, the charging module 150 can comprise a form factor of a headwear (e.g., hat, cap, earphone, etc.) stand, such that placing the system 100, coupled to the user's headwear accessory, on the headwear accessory stand facilitates charging of the system 100. The charging module 150 can, however, comprise any other suitable form factor. Furthermore, the charging module 150 can be configured to charge an energy storage element of the intermediate region 140 in any other suitable manner.

Figure 4:
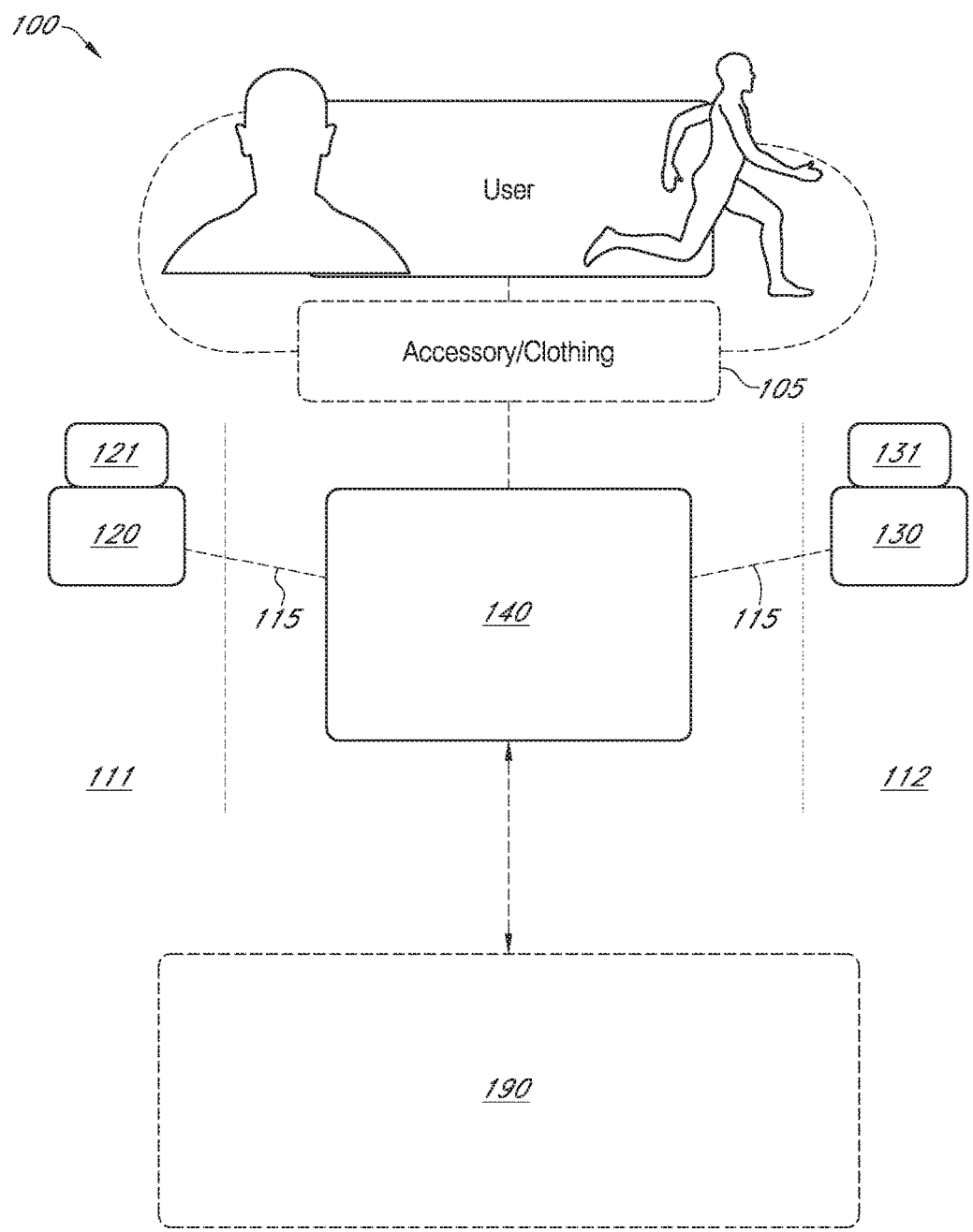
FIG. 4 illustrates a schematic block diagram of one embodiment of a system for detecting and analyzing biosignals.

In some embodiments, as shown in FIGS. 4-5, the system 100 may further include a user communications module 190 configured to interface with the intermediate region 140 in order to facilitate communication between a user and the system 100. The user communications module 190 may be configured to accept user input (e.g., physical taps, voice, applied pressure) locally or remotely (e.g., via cloud or server). In some embodiments, the user communications module 190 may alert the user to biologically relevant information (e.g. physiological conditions, characteristics). Additionally or alternatively, the user communications module 190 may provide non-biologically relevant information (e.g. the time, date, weather). The user communications module 190 can be a system component coupled to the system or a non-system component with which the system 100 communicatively couples. In one non-limiting example, the system 100 may couple to an optical head-mounted user interface display of a pair of smart glasses. In such embodiments, the system 100 may communicate with a non-system user interface to display notifications.

Methods

Figure 11:
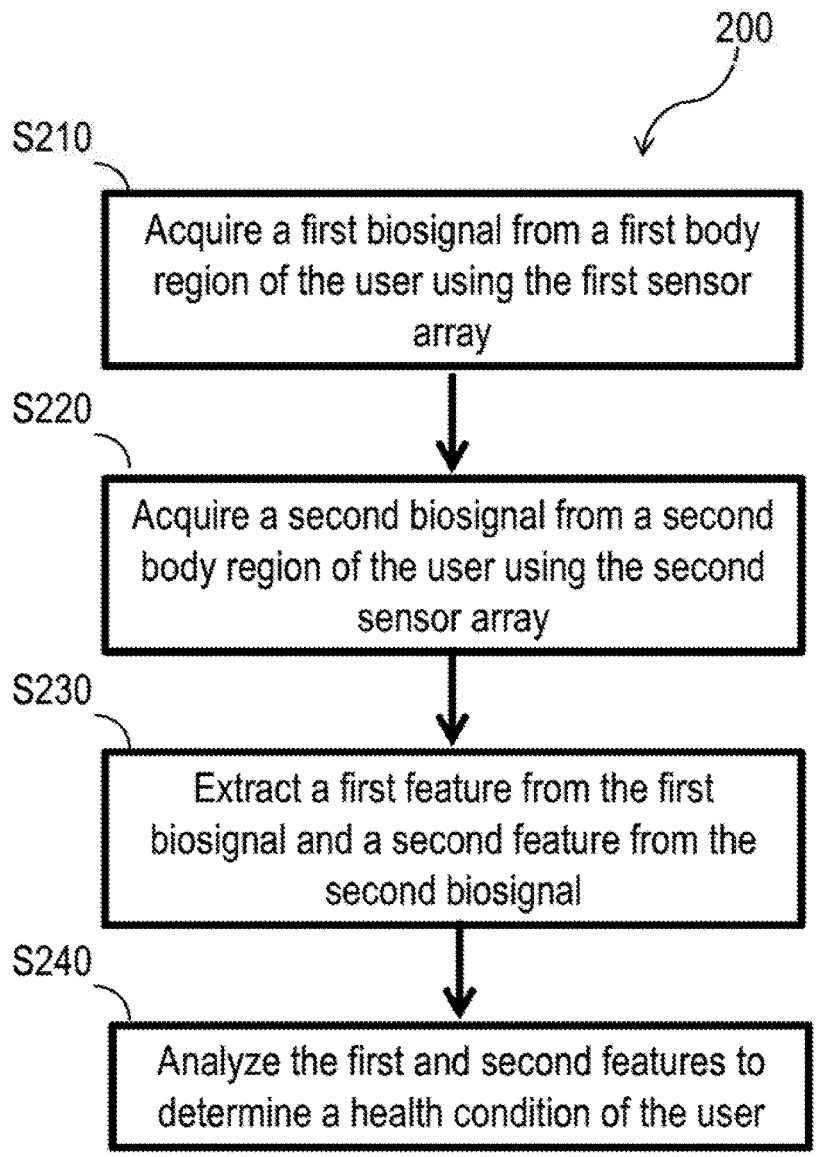
FIG. 11 illustrates one embodiment of a method of detecting and analyzing biosignals.

As shown in FIG. 11, one embodiment of a method for detecting and measuring biosignals includes acquiring a first biosignal from a first body region of the user using a first sensor array in block S210, acquiring a second biosignal from a second body region of the user using a second sensor array in block S220, extracting a first feature from the first biosignal and a second feature from the second biosignal in block S230, and analyzing the first and second features to determine a health condition of the user in block S240. The method functions to monitor a health condition of a user.

As shown in FIG. 11, one embodiment of a method for detecting and measuring biosignals includes blocks S210 and S220, which recite acquiring a first biosignal from a first body region of the user using a first sensor array and acquiring a second biosignal from a second body region of the user using a second sensor array, respectively. Blocks S210 and S220 function to acquire one or more biosignals from a user to determine a health condition of the user. In some embodiments, the first body region is a fixed distance from the second body region, for example the fixed distance between a user's ears. The fixed distance between the first and second sensor arrays improves measurement accuracy, reliability, repeatability, and analysis, especially in bioimpedance applications. In some embodiments, the first body region is contralateral or ipsilateral the second body region. In some embodiments, the first body region is the same as the second body region, for example in a variation in which there is one sensor array or two or more sensor arrays in close proximity. In some such embodiments, the first and second sensor arrays may be housed together in the first end region 111, the second end region 112, the intermediate region 140, along the housing 110, or along the coupling element 115.

In some embodiments, the first and/or second biosignals include one or more of: bioimpedance signals, temperature signals, pulse oximetry signals, blood flow, blood pressure, heart rate, heart rate variability, electrocardiography, electromyography, electroencephalography, galvanic skin response, magnetoencephalography impedance signals, acoustic signals, respiration signals, positional signals, hydration status signals, and caloric intake signals.

As shown in FIG. 11, one embodiment of a method for detecting and measuring biosignals includes block S230, which recites extracting a first feature from the first biosignal and a second feature from the second biosignal. Block S230 functions to extract patterns, characteristics, points of interest, etc. from the sensor signal to determine a health condition of the user. In some embodiments, the first and second features include one or more of: a blood volume; a skin water content; cardiac output; an average temperature; an instantaneous temperature; an oxygen saturation level; a heart rate; a heart rate variability; a heart electrical activity; a brain electrical activity; a muscle electrical activity; a stress level; a neuronal activity level; a depth of breadth; a respiration rate; thoracic variations; inspiratory flow characteristics; expiratory flow characteristics; a location or position of the user; a calorie intake; body fluid; pulse rate; blood flow; heartbeat signatures; cardio-pulmonary heath; organ heath; metabolism; electrolyte type and concentration; physical activity; caloric metabolism; metabolomics; physical and psychological stress levels and stress level indicators; physiological and psychological response to therapy; drug dosage and activity; physiological drug reactions; drug chemistry in the body; biochemistry; position and balance; body strain; blood pressure; cranial pressure; hydration level; physiological response to infection; eye muscle movement; physical exertion; exhaled breath physical and chemical composition; the presence, identity, and concentration of viruses and bacteria, foreign matter in the body; internal toxins; heavy metals in the body; anxiety; fertility; ovulation; sex hormones; psychological mood; sleep patterns; hunger and thirst; hormone type and concentration; cholesterol; lipids; bone density; body fat density; muscle density; organ and body weight; reflex response; sexual arousal; mental and physical alertness; sleepiness; response to external stimuli; swallowing volume; swallowing rate; sickness; voice characteristics (e.g., tone, pitch, volume, etc.); vital signs; head tilt; allergic reactions; inflammation response; DNA, proteins; protein levels in the blood; blood water content; pheromones; internal body sounds; digestive system functioning; cellular regeneration response; healing response; stem cell regeneration response; and the like.

As shown in FIG. 11, one embodiment of a method for detecting and measuring biosignals includes block S240, which recites analyzing the first and second features to determine a health condition of the user. Block S240 functions to examine one or more features to determine the health condition of the user. In some embodiments, analyzing includes reviewing the feature extracted from one sensor array to determine a health condition of the user. In some embodiments, analyzing includes comparing or combining two or more features extracted from one or more biosignals from one or more sensor arrays to determine a health condition of the user. The features may be extracted from one biosignal from one sensor array or from a plurality of biosignals or from two or more sensor arrays or a plurality of sensor arrays.

In some embodiments, the method includes identifying the health condition as one of: a heart-related condition, a muscle-related condition, a neurological condition, and an organ-specific condition (e.g., heart failure, kidney failure, pleural effusion, seizure, etc.). In some embodiments, the method includes identifying the health condition as one of: a stroke, a seizure, a migraine, hemiparesis, hemiplegia, hemispatial, heart failure, myocardial infarction, septicemia, pneumonia, cerebrovascular disease, chronic obstructive pulmonary disease, diabetes, atherosclerosis, heart disease, kidney disease, liver disease, dehydration, fluid overload, electrolyte derangements, pleural effusion, and lymphedema (i.e., swelling due to lymphatic system blockage).

In some embodiments, the method includes monitoring the health condition over time using one or more of the first and second sensor arrays; and identifying a change in the health condition over time. In some such embodiments, the system or a healthcare provider may recommend certain actions by the user to change his/her health condition. The system may monitor the health condition of the user over time to determine if the recommendation is improving or worsening the health condition of the user. Alternatively, the system may monitor the health condition of the user pre-release from a hospital and post-release to determine if the health condition of the user is stable, worsening, or improving over time, and, in some embodiments, to determine if hospital readmission is necessary.

In some embodiments, identifying a change in the health condition of the user over time includes comparing a baseline health condition of the user, for example pre-hospital admittance, to a current health condition of the user, for example post-surgery or post-hospital release. In some embodiments, identifying a change in the health condition of the user over time includes comparing a current health condition of the user to a population average, regional average, or other pertinent average.

In some embodiments, the method may include: amplifying, filtering, digitizing, and/or otherwise processing the sensor signal to isolate a readable signal from a noisy acquired signal. In some such embodiments, digitizing may include transforming an electrical signal (e.g., resistance, voltage, impedance, or capacitance), produced by an embodiment of the sensor arrays described elsewhere herein, into a set of quantitative parameters. For example, a set of quantitative parameters may be generated at time points within a given time window (e.g., during which electrophysiological signals are received), in order to facilitate generation of a trend in a metric, based upon at least one characteristic characterizing the user's health condition.

In some embodiments, the method may further comprise displaying the biosignal data on a computing device. In one embodiment, the biosignal is displayed graphically, numerically, as a picture, or any other representation. In some embodiments, the displayed biosignal is updated over time In some embodiments, the method includes alerting or notifying a user (e.g., healthcare provider, emergency response team, partner, spouse, etc.) of a deviation from normal parameters of a user's health condition. For example, a user experiences an illness and this change in condition is transmitted to a designated user or system.

Figure 12:
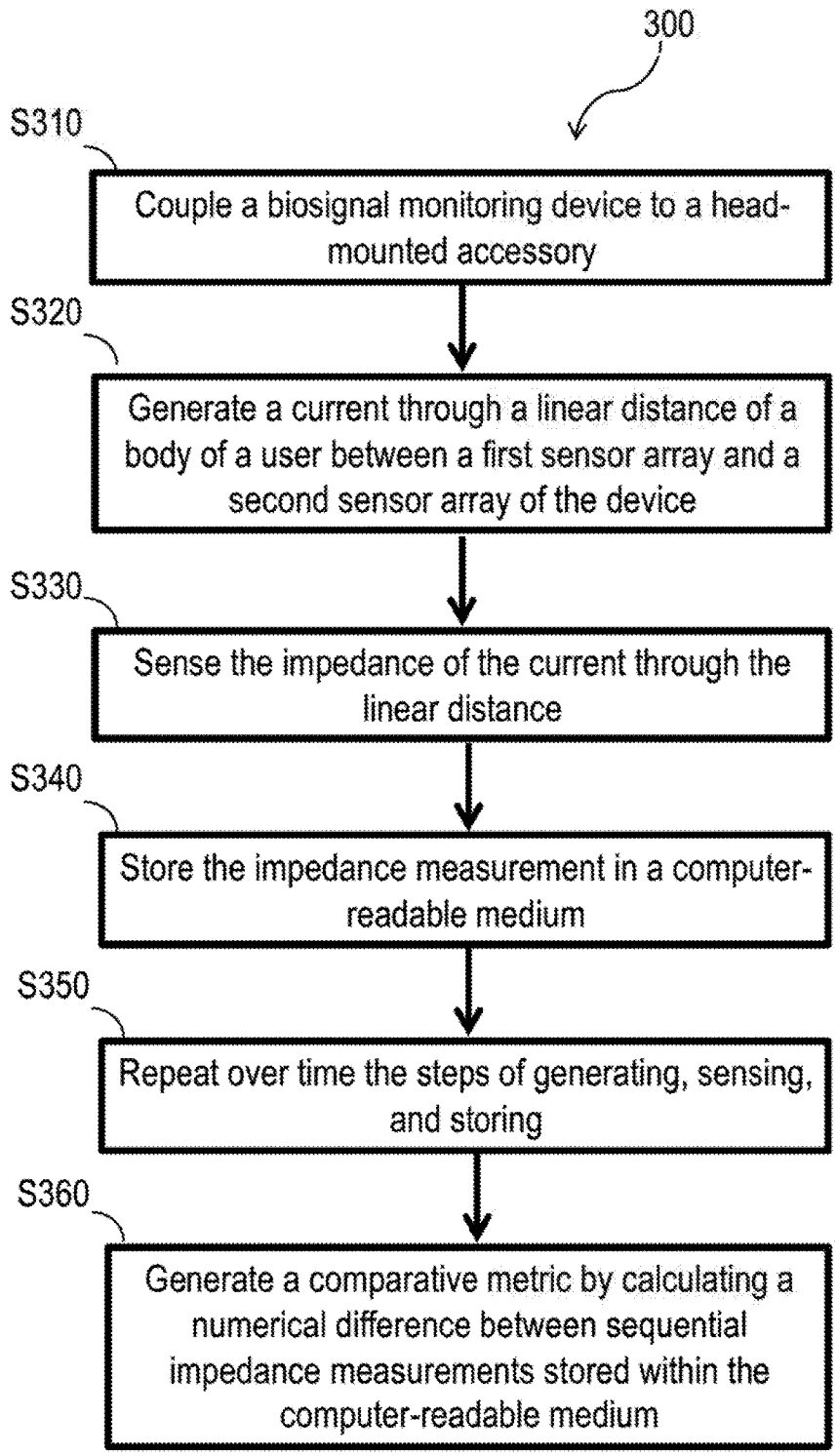
FIG. 12 illustrates one embodiment of a method to achieve daily physiological monitoring of ionic fluid content within a user.

As shown in FIG. 12, one embodiment of a method 300 to achieve daily physiological monitoring of ionic fluid content within a user comprises: coupling a biosignal monitoring device to a head-mounted accessory S310; generating a current through a linear distance of a body of a user between a first sensor array and a second sensor array of the biosignal monitoring device 8320; sensing an impedance of the current through the linear distance S330; storing the impedance measurement in a computer-readable medium S340; repeating over time the steps of generating, sensing, and storing S350; and generating a comparative metric by calculating a numerical difference between sequential impedance measurements stored within the computer-readable medium S360. In some embodiments, information derived from the method 300 can be conveyed or provided to a user by a healthcare provider to achieve daily physiological monitoring of ionic fluid content changes within the body of the user. However, method 300 can be configured to achieve monitoring of any sort of biosignal from between or around the tissue of the head, whether short or long term. Method 300 functions to enable improved patient compliance with daily monitoring of biosignals over time, without disrupting daily habits, and is preferably intended for use outside of a clinical/research setting. Alternatively, method 300 may be configured to be used inside of a clinical/research setting and may also be used for monitoring health conditions over short periods of time.

As shown in FIG. 12, one embodiment of a method to achieve daily physiological monitoring of ionic fluid content within a user includes block 8310, which recites coupling a biosignal monitoring device to a head-mounted accessory. In some embodiments, S310 may be implemented by coupling a physiological monitoring device comprising first and second sensor arrays that sense biometric signals to a user's eyewear. The first sensor array may be coupled to a first leg or temple region, and the second sensor array may be coupled to the second leg or temple region, such that the first sensor array is contralateral to the second sensor array on the opposite side of the head of the user when the eyewear is worn. In some embodiments, S310 may be implemented such that the sensor-user interfaces formed by the first and second sensor arrays and the user are proximal to a region of contact between the pinna region of the ear and the temporal bone behind the ear of the user. However, the device may be coupled to the eyewear by any suitable means.

As shown in FIG. 12, one embodiment of a method to achieve daily physiological monitoring of ionic fluid content within a user includes block S320, which recites generating a current through a linear distance of a body of a user between a first sensor array and a second sensor array of the biosignal monitoring device. In some embodiments, S320 functions to generate a current through a linear distance of a body of a user between the first and second sensor arrays. In some such embodiments, the distance between the two sensor arrays is less than one foot and spans a linear length through the head of the user.

As shown in FIG. 12, one embodiment of a method to achieve daily physiological monitoring of ionic fluid content within a user includes blocks S330 and S340, which recite sensing an impedance of the current through the linear distance; and storing the impedance measurement in a computer-readable medium, respectively. In some embodiments, S330 functions to sense an impedance of the current through the linear distance, thereby providing a measurement that can be used to determine ionic fluid content within the body of a user. In some embodiments, S340 functions to store the impedance measurement in a computer-readable medium to be simultaneously or consecutively processed by a processor of the system.

As shown in FIG. 12, one embodiment of a method to achieve daily physiological monitoring of ionic fluid content within a user includes block S350, which recites repeating over time the steps of generating, sensing, and storing. In some embodiments, S350 functions to generate additional measurements over time to determine a health condition of the user. The accuracy, reliability, and repeatability of these measurements are improved over time by the consistent placement of the sensor arrays on the head of the user when the system is coupled to a head-mounted accessory of the user. In some embodiments, the measurements are taken automatically or manually. In some embodiments, the measurements taken over time represent time points, for example defined by a healthcare provider, each time point spaced from prior and subsequent time points by fixed or random intervals of time, thereby generating and storing a sequence of impedance measurements over time. Alternatively, in some embodiments, each time point representing a measurement is taken randomly or based on user input. However, these measurements may alternatively be recorded continuously and in real time. S350 functions to collect and record a large dataset with which to analyze in S360. However, in some variations, S360 may be performed concurrently with the collection of measurements in S350.

As shown in FIG. 12, one embodiment of a method to achieve daily physiological monitoring of ionic fluid content within a user includes block S360, which recites generating a comparative metric by calculating a numerical difference between sequential impedance measurements stored within the computer-readable medium. In some embodiments, S360 functions to calculate a numerical difference or a plurality of numerical differences between sequential impedance measurements stored within the computer-readable medium by subtracting the impedance measurement recorded at a time point, t, from the impedance measurement recorded from the time point prior to t, t−1, for all time points. S360 functions to determine changes in impedance, and thus effectively serves to monitor fluid status over time. Once baseline or average values of impedance have been established, a comparative metric may be used to alert the user or healthcare provider about significant changes in the measurements, and may ultimately assist in leading to conclusions about a health condition of the user, and suggestions for how to improve the health condition of the user.

Figure 13:
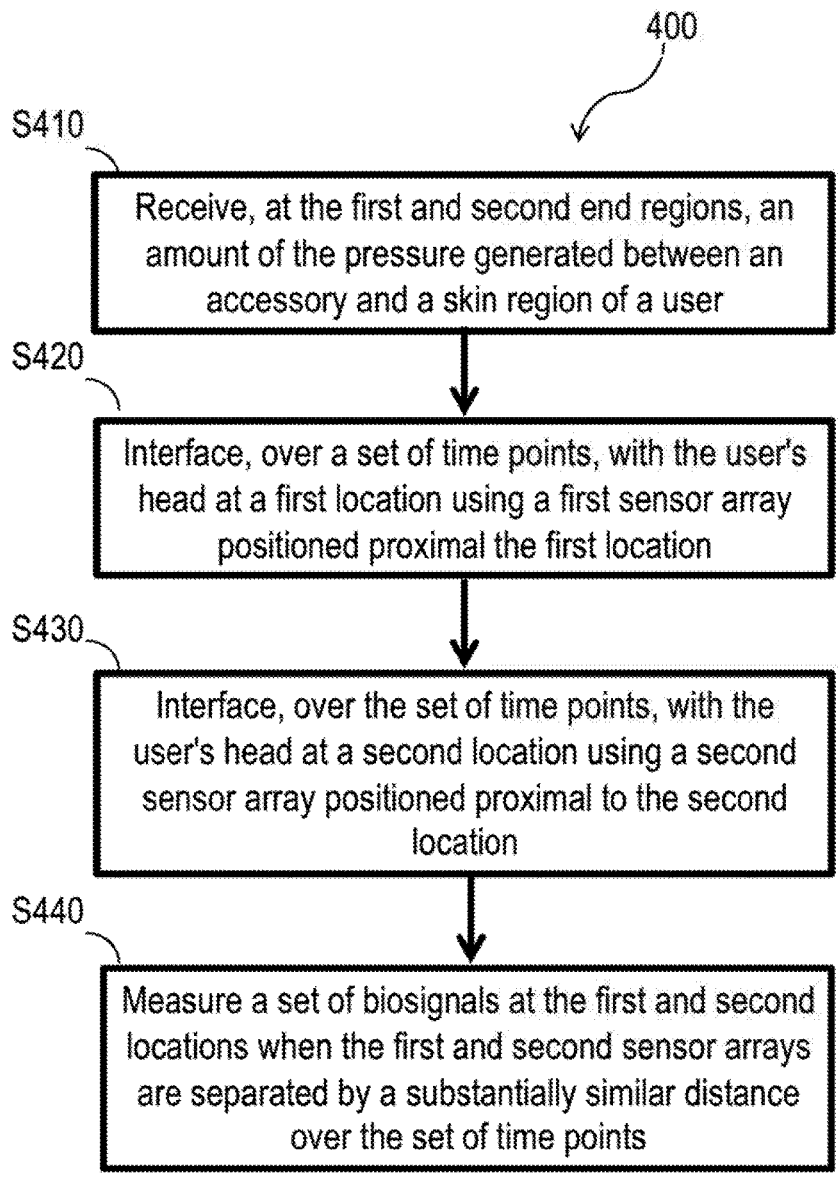
FIG. 13 illustrates one embodiment of a method of measuring biosignals of a user.

As shown in FIG. 13, one embodiment of a method 400 for measuring biosignals of a user includes: receiving, at first 111 and second 112 end regions, an amount of the pressure generated between the accessory and a skin region of a user S410; interfacing, over a set of time points, with the user's head at a first location using a first sensor array positioned proximal the first location S420; interfacing, over the set of time points, with the user's head at a second location using a second sensor array positioned proximal to the second location S430; and measuring a set of biosignals at the first and second locations when the first and second sensor arrays are separated by a substantially similar distance over the set of time points S440. The method functions to monitor biosignals of a user, and can further function to inform a user of medically relevant metrics upon which specific actions may be recommended to the user and performed by the user.

As shown in FIG. 13, one embodiment of a method 400 for measuring biosignals of a user includes block S410, which recites receiving, at the first 111 and second 112 end regions, an amount of the pressure generated between an accessory and a skin region of a user. Block S410 functions to receive an amount of user-generated or accessory-generated pressure in order to sustain the sensor arrays in substantially the same location over a set of time points.

As shown in FIG. 13, one embodiment of a method 400 for measuring biosignals of a user includes blocks S420 and S430, which recite interfacing, over a set of time points, with the user's head at a first location using a first sensor array positioned proximal the first location; and interfacing, over the set of time points, with the user's head at a second location using a second sensor array positioned proximal to the second location, respectively. Blocks S420 and S430 function to interface with the user, through two sensor arrays, each at the same location on the user's body over a series of time points. In some embodiments, the point of contact between the system and the user is at the medial side of the area proximal to the user's left or right posterior ear region. Alternatively, the interfacing with the user can occur at any suitable body location.

As shown in FIG. 13, one embodiment of a method 400 for measuring biosignals of a user includes block S440, which recites measuring a set of biosignals at the first and second locations when the first and second sensor arrays are separated by a substantially similar distance over the set of time points. Block S440 functions to measure a particular set of biosignals when the first and second sensor arrays are separated by a substantially similar distance across measurements of the biosignals over time. In some embodiments, the substantially similar separation distance between the first and second sensor arrays over time is approximately the separation distance between the first location and the second location. Alternatively, in some embodiments, the substantially similar separation distance is larger than the distance between the first and second locations.

In some embodiments, the method includes measuring the biosignals upon manual user activation (e.g., through voice, a button, remote device). In some embodiments, the method further includes measuring biosignals upon detecting an event or trigger or at different rates depending on circumstances such as remaining electrical power or additional information regarding the user's biosignals, characteristics, health conditions, or activities.

In some embodiments, the method may include receiving, using a supplementary sensor array 145, a set of supplementary signals representing user data; and associating the set of supplementary signals with data based on the set of measured biosignals.

In some embodiments, the method may further comprise generating a medically relevant metric based on an analysis of data associated with the set of measured biosignals. Generating a medically relevant metric functions to generate data representing biological characteristics, conditions, or recommendations for a user based on analysis of data associated with the set of measured biosignals. In some embodiments, generating medically relevant metrics occurs through applications of machine learning algorithms (e.g., supervised, unsupervised, neural networks) configured to identify biosignal signatures of the user. In some such embodiments, the machine learning algorithms incorporate the supplemental user data in generating the medically relevant metric. In one non-limiting example, the system may generate a recommendation for the user to drink water and sit down, where the recommendation resulted from an analysis of historical user data and biosignals. In this example, the recommendation was generated based on a determination that the user was at a lower fluid status and a higher heart rate compared to what the system 100 recorded in the past for this user performing a specific activity (e.g., walking).

In some embodiments, the method may further comprise notifying the user of a medically relevant metric at a user communications module. In some embodiments, the notification comes in the form of a visual signal (e.g. a pop up on a mobile device, the flashing of a user communications module, etc.), a haptic signal (e.g., unobtrusive vibration), or an auditory signal (e.g., beep, buzz, ding, music, etc.). However, the notification can come in any suitable form. In some embodiments, the system automatically notifies the user. In some embodiments, the system notifies the user based off manual user-set configurations and inputs (e.g. setting a daily notification to lower heart rate through meditation). Any notification that occurs to the user at communications modules also may be electively shared with a designated third party such as a caretaker, healthcare provider, or family member.

The systems and methods of the preferred embodiment and variations thereof can be embodied and/or implemented at least in part as a machine configured to receive a computer-readable medium storing computer-readable instructions. The instructions are preferably executed by computer-executable components preferably integrated with the system 100 and one or more portions of the processor and/or a controller. The computer-readable medium can be stored on any suitable computer-readable media such as RAMs, ROMs, flash memory, EEPROMs, optical devices (CD or DVD), hard drives, floppy drives, or any suitable device. The computer-executable component is preferably a general or application specific processor, but any suitable dedicated hardware or hardware/firmware combination device can alternatively or additionally execute the instructions.

As used in the description and claims, the singular form "a", "an" and "the" include both singular and plural references unless the context clearly dictates otherwise. For example, the term "sensor array" may include, and is contemplated to include, a plurality of sensor arrays. At times, the claims and disclosure may include terms such as "a plurality," "one or more," or "at least one;" however, the absence of such terms is not intended to mean, and should not be interpreted to mean, that a plurality is not conceived.

The term "about" or "approximately," when used before a numerical designation or range (e.g., to define a length or pressure), indicates approximations which may vary by (+) or (−) 5%, 1% or 0.1%. All numerical ranges provided herein are inclusive of the stated start and end numbers. The term "substantially" indicates mostly (i.e., greater than 50%) or essentially all of a system or method.

As used herein, the term "comprising" or "comprises" is intended to mean that the systems and methods include the recited elements, and may additionally include any other elements. "Consisting essentially of" shall mean that the systems and methods include the recited elements and exclude other elements of essential significance to the combination for the stated purpose. Thus, a system or method consisting essentially of the elements as defined herein would not exclude other materials, features, or steps that do not materially affect the basic and novel characteristic(s) of the claimed disclosure. "Consisting of" shall mean that the systems and methods include the recited elements and exclude anything more than a trivial or inconsequential element or step. Embodiments defined by each of these transitional terms are within the scope of this disclosure.

The figures illustrate the architecture, functionality and operation of possible implementations of systems, methods and computer program products according to preferred embodiments, example configurations, and variations thereof. In this regard, each block in the flowchart or block diagrams may represent a module, segment, or portion of code, which comprises one or more executable instructions for implementing the specified logical function(s). It should also be noted that, in some alternative implementations, the functions noted in the block can occur out of the order noted in the figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts, or combinations of special purpose hardware and computer instructions.

The examples and illustrations included herein show, by way of illustration and not of limitation, specific embodiments in which the subject matter may be practiced. Other embodiments may be utilized and derived therefrom, such that structural and logical substitutions and changes may be made without departing from the scope of this disclosure. Such embodiments of the inventive subject matter may be referred to herein individually or collectively by the term "invention" merely for convenience and without intending to voluntarily limit the scope of this application to any single invention or inventive concept, if more than one is in fact disclosed. Thus, although specific embodiments have been illustrated and described herein, any arrangement calculated to achieve the same purpose may be substituted for the specific embodiments shown. This disclosure is intended to cover any and all adaptations or variations of various embodiments. Combinations of the above embodiments, and other embodiments not specifically described herein, will be apparent to those of skill in the art upon reviewing the above description.

What is claimed is:

1. A system for monitoring biosignals of a user, the system comprising:
    a first end region, positionable on one of an area posterior and an area superior to a first ear of a user, comprising a first sensor array;
    a second end region, positionable on one of an area posterior and an area superior to a second ear of the user, comprising a second sensor array;
    an intermediate region, positionable on a back of a neck region of the user, wherein the intermediate region comprises an analog to digital converter for receiving and digitizing biosignals acquired by the first and second sensor arrays, a processor configured to perform an analysis and translation of the digitized biosignals into physiological measurement data, a transmission module configured to perform signal transmission, and a power module configured to supply power to the system;
    a coupling element configured to couple the first and second end regions to the intermediate region; and
    a first attachment element and a second attachment element, wherein the first attachment element couples the first end region to a head-mounted accessory and the second attachment element couples the second end region to the head-mounted accessory.

2. The system of claim 1, wherein each attachment element comprises a sleeve defining an aperture configured to slidably receive a temple or temple end of the head-mounted accessory.

3. The system of claim 2, wherein a diameter of the aperture defined by the sleeve is adjustable.

4. The system of claim 1, wherein the coupling element electrically and physically couples the first and second end regions to the intermediate region.

5. A system for monitoring biosignals of a user accurately, reliably, and reproducibly, the system comprising:

a first end region, positionable on one of an area posterior and an area superior to a first ear of a user, comprising a first sensor array;

a second end region, positionable on one of an area posterior and an area superior to a second ear of the user, comprising a second sensor array, wherein there is a fixed linear distance between the first sensor array and the second sensor array;

an intermediate region, positionable on a back of a neck region of the user;

a coupling element configured to couple the first and second end regions to the intermediate region;

a first attachment element and a second attachment element, wherein the first attachment element couples the first end region to a head-mounted accessory and the second attachment element couples the second end region to the head-mounted accessory; and a processor and a computer-readable medium having non-transitory, processor-executable instructions stored thereon, wherein execution of the instructions causes the processor to perform a method comprising:

generating a current through the fixed linear distance of a body of the user, sensing an impedance of the current through the fixed linear distance, storing the impedance measurement in the computer-readable medium, repeating over time the steps of generating, sensing, and storing, and generating a consistent, comparative metric between sequential impedance measurements stored within the computer-readable medium.

6. The system of claim 1, wherein the first sensor array and the second sensor array are configured to cooperatively detect an impedance of an applied current along a distance separating the first sensor array and the second sensor array, thereby providing a measurement of ionic fluid content within the user.

7. The system of claim 1, further comprising the head-mounted accessory, wherein the head-mounted accessory is one of: eyeglasses, sunglasses, goggles, and bifocals.

8. The system of claim 6, wherein the first and second sensor arrays are integrated into the head-mounted accessory.

9. The system of claim 1, further comprising a processor and a computer-readable medium having non-transitory, processor-executable instructions stored thereon.

10. The system of claim 9, wherein the processor is integrated into one of the first end region, the second end region, and the intermediate region.

11. The system of claim 9, wherein execution of the instructions of the computer-readable medium causes the processor to perform a method comprising:

acquiring a first biosignal from a first body region of the user using the first sensor array, acquiring a second biosignal from a second body region of the user using the second sensor array, extracting a first feature from the first biosignal and a second feature from the second biosignal, and analyzing the first and second features to determine a health condition of the user.

12. The system of claim 11, wherein the method performed by the processor further comprises:

monitoring the health condition over time using one or more of the first and second sensor arrays; and identifying a change in the health condition over time.

13. The system of claim 11, wherein the first and second biosignals include one or more of: bioimpedance signals, temperature signals, pulse oximetry signals, blood flow, blood pressure, heart rate, heart rate variability, electrocardiography, electromyography, electroencephalography signals, galvanic skin response, magnetoencephalography impedance signals, acoustic signals, respiration signals, positional signals, and caloric intake signals.

14. The system of claim 11, wherein the first and second features include one or more of: a blood volume, a blood pressure, a skin water content, cardiac output, an average temperature, an instantaneous temperature, an oxygen saturation level, a heart rate, a heart rate variability, a heart electrical activity, a brain electrical activity, a muscle electrical activity, a stress level, a neuronal activity level, a depth of breadth, a respiration rate, thoracic variations, inspiratory flow characteristics, expiratory flow characteristics, vocal sounds, a location of the user, and a calorie intake amount.

15. The system of claim 11, wherein the method performed by the processor further includes:

transmitting, using an antenna, one or more of the first and second features to a healthcare provider.

16. The system of claim 11, wherein the first body region is contralateral the first sensor array and the second body region is contralateral the second sensor array.

17. The system of claim 11, wherein the first body region is ipsilateral the first sensor array and the second body region is ipsilateral the second sensor array.

18. The system of claim 11, wherein the first body region is the same as the second body region.

19. A system for monitoring biosignals of a user, the system comprising:

a first end region, positionable on one of an area posterior and an area superior to a first ear of a user, comprising a first sensor array;

a second end region, positionable on one of an area posterior and an area superior to a second ear of the user, comprising a second sensor array;

an intermediate region, positionable on a back of a neck region of the user, wherein the intermediate region comprises a processor configured to perform an analysis of the biosignals, a power module configured to supply power to the system, and a third sensor array;

a coupling element configured to couple the first and second end regions to the intermediate region; and a first attachment element and a second attachment element, wherein the first attachment element couples the first end region to a head-mounted accessory and the second attachment element couples the second end region to the head-mounted accessory.

20. The system of claim 5, wherein the fixed linear distance is a distance between two ears of the user that measures less than one foot.

* * * * *